(12) United States Patent
Doebler et al.

(10) Patent No.: US 11,479,747 B2
(45) Date of Patent: Oct. 25, 2022

(54) ARRAYED LYSER AND HOMOGENIZER SYSTEMS WITH MULTIPLE AGITATOR DEVICES

(71) Applicant: CLAREMONT BIOSOLUTIONS LLC, Upland, CA (US)

(72) Inventors: Robert W. Doebler, Upland, CA (US); Mark Brown, Yorba Linda, CA (US); Tanya Ferguson, Pasadena, CA (US); Bruce Irvine, Concord, CA (US); James D. Sterling, Upland, CA (US)

(73) Assignee: CLAREMONT BIOSOLUTIONS LLC, Upland, CA (US)

( * ) Notice: Subject to any disclaimer, the term of this patent is extended or adjusted under 35 U.S.C. 154(b) by 60 days.

(21) Appl. No.: 16/483,363

(22) PCT Filed: Feb. 1, 2018

(86) PCT No.: PCT/US2018/016442
§ 371 (c)(1),
(2) Date: Aug. 2, 2019

(87) PCT Pub. No.: WO2018/144723
PCT Pub. Date: Aug. 9, 2018

(65) Prior Publication Data
US 2020/0010789 A1    Jan. 9, 2020

Related U.S. Application Data

(60) Provisional application No. 62/454,500, filed on Feb. 3, 2017.

(51) Int. Cl.
*C12M 1/06* (2006.01)
*B01L 3/00* (2006.01)
*C12M 1/00* (2006.01)

(52) U.S. Cl.
CPC ........... *C12M 27/02* (2013.01); *B01L 3/5085* (2013.01); *C12M 47/06* (2013.01); *C12M 47/08* (2013.01); *B01L 2200/0647* (2013.01)

(58) Field of Classification Search
CPC ...... C12M 27/02; C12M 47/06; C12M 47/08; C12M 1/33; C12M 35/06; C12N 1/066;
(Continued)

(56) References Cited

U.S. PATENT DOCUMENTS

| | | | |
|---|---|---|---|
| 6,547,943 B1 * | 4/2003 | Kane | G01N 27/44743 204/453 |
| 2006/0133968 A1 * | 6/2006 | Dales | B01J 19/0006 422/130 |

(Continued)

FOREIGN PATENT DOCUMENTS

| | | | | |
|---|---|---|---|---|
| GB | 703344 A | * | 2/1954 | ............ C12M 27/02 |
| GB | 703344 A | | 2/1954 | |
| WO | 2016/168301 A1 | | 10/2016 | |

OTHER PUBLICATIONS

International Search Report and Written Opinion for PCT Application No. PCT/US2018/016442 dated Apr. 12, 2018.

*Primary Examiner* — Michael L Hobbs
*Assistant Examiner* — Lenora A Abel
(74) *Attorney, Agent, or Firm* — Seed Intellectual Property Law Group LLP

(57) ABSTRACT

Systems and methods for the efficient agitation of tissue samples. A device may include a plurality of chambers that each receives samples therein. The plurality of chambers may be uniformly spaced with respect to a least one dimension, to form a one dimensional or two dimensional array. Each of the chambers may include an opening and an agitator device in fluid contact with the sample disposed within the chamber. The agitator devices may include a micromotor which provides rotational motion to a shaft and
(Continued)

an impeller fixed to the shaft such that the impeller and the shaft rotate together upon provision of the rotational motion by the micromotor. The system may include an electrical energy source electrically coupled to the plurality of micromotors to rotate the impellers sufficient to agitate the sample as required for a particular activity (e.g., homogenization, lysis).

12 Claims, 23 Drawing Sheets

(58) Field of Classification Search
CPC ... C12N 1/06; C12N 15/01; B01L 2400/0487; B01L 2200/0647
USPC ........................................................ 435/306.1
See application file for complete search history.

(56) References Cited

U.S. PATENT DOCUMENTS

| | | | |
|---|---|---|---|
| 2010/0034048 A1* | 2/2010 | Jagle | B01F 13/1038 366/118 |
| 2013/0334120 A1 | 12/2013 | Ingber et al. | |
| 2014/0127773 A1* | 5/2014 | Brown | C12M 47/06 435/174 |

* cited by examiner

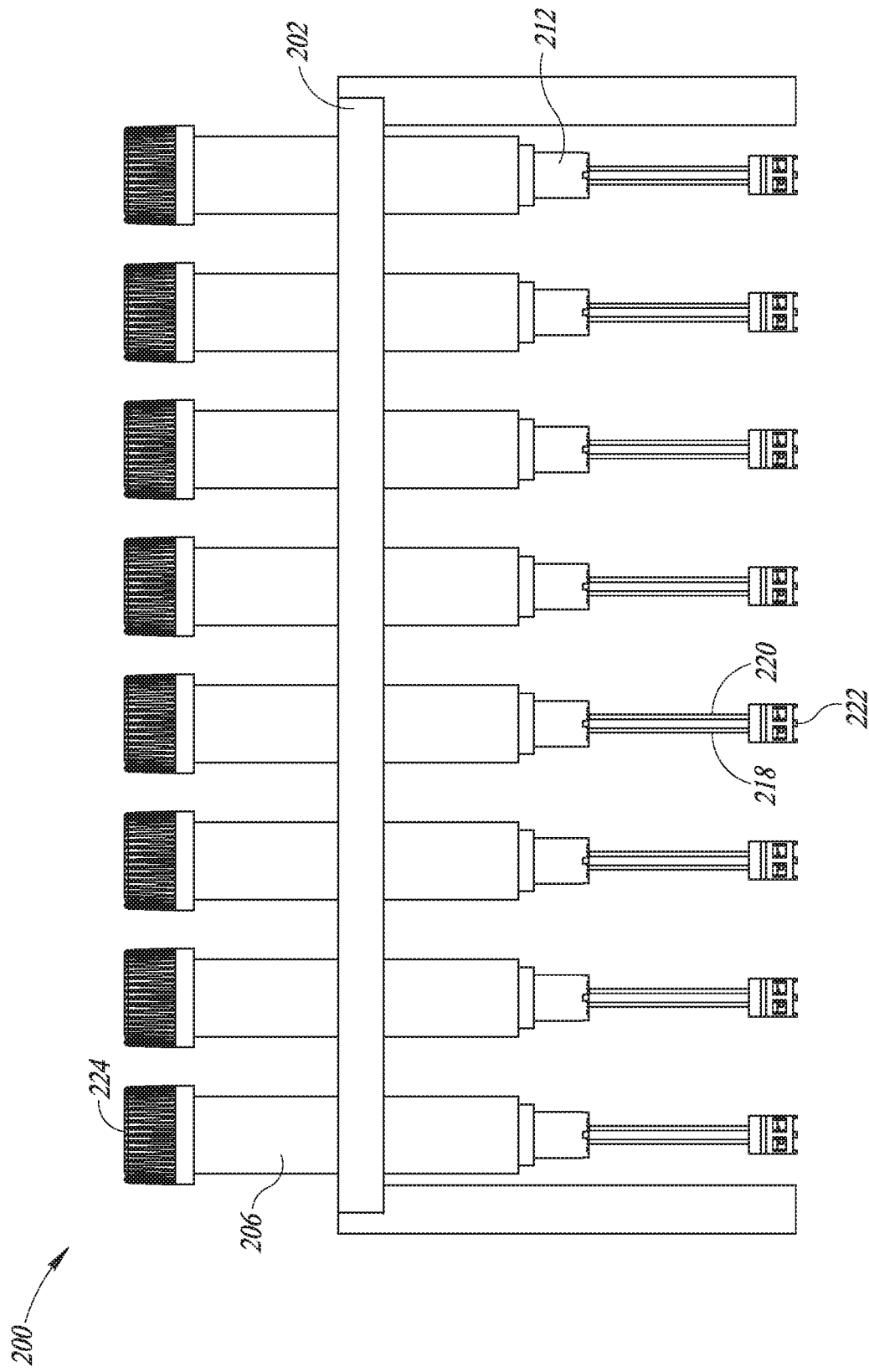

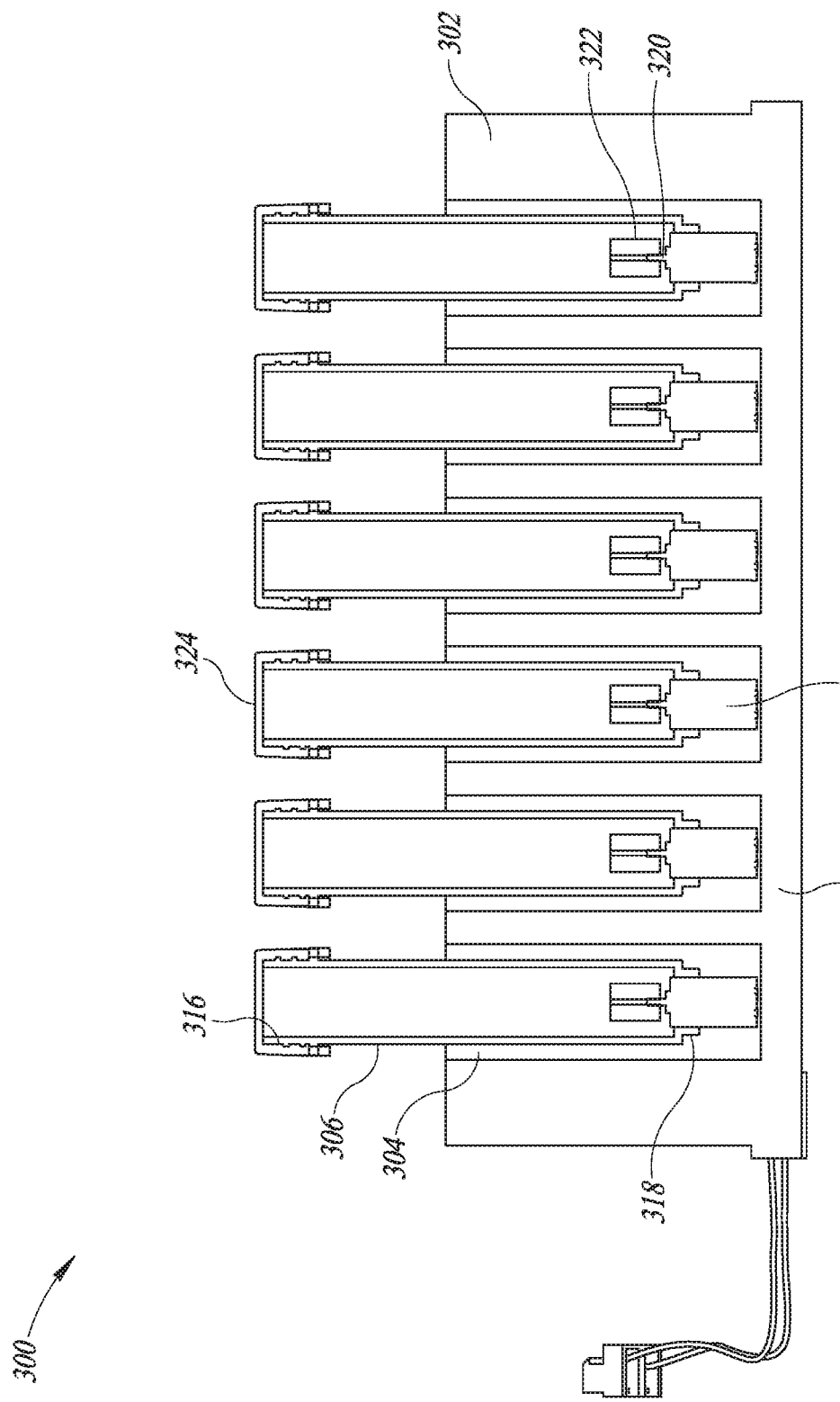

ARRAYED LYSER AND HOMOGENIZER SYSTEMS WITH MULTIPLE AGITATOR DEVICES

BACKGROUND

Technical Field

The present disclosure generally relates to preparation of samples for analysis, and in particular to lyser and homogenizer systems.

Description of the Related Art

Processing of biological specimens, for example cell lysis, is used to provide biological materials for compositional analysis. Specific biological materials may include proteins, lipids, and nucleic acids either individually or as complexes. For example, when a cell membrane is lysed, certain organelles—nuclei, mitochondria, lysosomes, chloroplasts, and/or endoplasmic reticulum—may be isolated. Such may be analyzed using methods such as polymerase chain reaction (PCR), electron microscopy, Western blotting or other analysis techniques.

There are numerous approaches to performing lysis. For example, enzymatic approaches may be employed to remove cell walls using appropriate enzymes in preparation for cell disruption or to prepare protoplasts. Another approach employs detergents to chemically disrupt cell membranes. These chemical approaches may adversely affect the resulting product, for example degrading the bio-products being released. Consequently, chemical approaches may, in some instances, not be practical. Yet another approach employs ultrasound to produce cavitation and impaction for disrupting the cells. Such an approach may not achieve as high a lysis efficiency as may be required or desired for many applications.

Yet still another approach employs beads (e.g., glass or ceramic) which are agitated, for example, via a vortex mixer. Such an approach successfully addresses the issues raised by chemical lysis approaches, yet improvements in such an approach are desirable.

The biology of cells may be examined in cell monolayer culture applications, however, they have inherent limitations for studying the effects of and screening for drugs and predicting in vivo physiological responses. As is known in the art, in vitro single cells or cell monolayer behave very differently from an in vivo organization of cells, wherein the cells are organized in a sophisticated cellular network and form tissues. In those networks, cellular responses of individual cells to drugs may be, at least to a certain extent, controlled by its extracellular environment within such network or tissue. Such extra-cellular environment, for example, includes cell-cell interaction and cell-matrix interactions. Particularly, cell-matrix interactions play an important role in the formation of tumors and progression of tumors.

Applicant has determined it is particularly desirable to provide for drug validation and drug screening assays using cell aggregates or tissue fragments, which mimic more the physiological environment from where they are obtained than single cells. As such, the applicant has identified a long felt need in the art to provide compositions and methods for the preparation of cell aggregates and/or tissue fragments which more accurately reflect the in vivo structure of a tissue, and more specifically, the in vivo structure of a cancerous tissue.

BRIEF SUMMARY

A system for homogenization and lysis of biological samples may be summarized as including a plurality of chambers spaced apart from each other in an array along at least a first dimension, each of the plurality of chambers sized and dimensioned to receive fluid and a biological sample therein; and a plurality of agitator devices each of which correspond to one of the plurality of chambers, at least a portion of each of the plurality of agitator devices positionable within the corresponding one of the plurality of chambers, and in operation each of the plurality of agitator devices selectively agitates the fluid and biological sample disposed in the corresponding one of the plurality of chambers. The plurality of chambers may be uniformly spaced apart from each other in a second dimension orthogonal to the first dimension. The plurality of chambers may be uniformly spaced apart from each other in the first dimension by a first distance which extends between the center of adjacent chambers along the first dimension, and the plurality of chambers may be uniformly spaced apart from each other in the second dimension by a second distance which extends between the center of adjacent chambers along the second dimension, wherein the first distance may be different than the second distance. The plurality of chambers may be uniformly spaced apart from each other in the first dimension by a first distance which may extend between the center of adjacent chambers along the first dimension, and the first distance may be equal to 4.5 millimeters (mm), 6 mm, 6.35 mm, 9 mm, 10 mm, 12 mm, 12.7 mm, 13 mm, 13.5 mm, 16 mm, or 18 mm. Each of the plurality of agitator devices may include a motor and an impeller that may be positionable at least partially in the corresponding chamber, the impeller coupled to the motor to be rotatably driven thereby. The plurality of chambers may be defined by a housing which may include a plurality of openings therein, each of the openings defining a respective one of the plurality of chambers.

The system wherein the plurality of agitators may include a plurality of micromotors each having a shaft and an impeller coupled to the shaft may be summarized as including a motor carrier that supports the plurality of micromotors, wherein each of the impellers is disposed at least partially within one of the plurality of chambers when the motor carrier is disposed proximate the housing. The impellers may be disposed at least partially within one of the plurality of chambers at a top opening thereof when the motor carrier is disposed proximate the housing. Each of the impellers may be disposed at least partially within one of the plurality of chambers at a bottom opening thereof when the motor carrier is disposed proximate the housing. The plurality of chambers may include a plurality of containers disposed in a support rack which may include a plurality of uniformly spaced openings, each of the openings receives one of the plurality of containers therein. Each of the plurality of agitator devices may be insertable into a respective one of the plurality of chambers via at least one of a top opening or a bottom opening of the chamber. At least a portion of each of the plurality of agitator devices may be fixed within a corresponding one of the plurality of chambers. At least a portion of each of the plurality of agitator devices may be selectively positionable within a corresponding one of the plurality of chambers.

The system may further include a medium that includes a particulate material and a fluid, the medium disposed within at least some of the plurality of chambers. The particulate material may include at least one of ceramic, glass, zirconia, zirconia/silica, zirconium silicate, metal, plastic, nickel, tungsten, tungsten carbide, yttrium stabilized zirconia, or sand.

A system may be summarized as including a plurality of uniformly spaced chambers to receive fluid and a biological sample therein, each of the plurality of chambers including at least a first opening to receive the fluid and the biological sample; and an agitator device in fluid contact with the fluid and the biological sample, the agitator device including a micromotor which provides rotational motion to a shaft extending from an interior of the micromotor, and an impeller fixed to the shaft such that the impeller and the shaft rotate together upon provision of the rotational motion by the micromotor; and an electrical energy source electrically coupled to the micromotor, the electrical energy source provides electrical energy to the micromotor sufficient to rotate the shaft and the impeller in a manner sufficient to agitate the biological sample. The first opening in each of the plurality of chambers removably may receive the agitator device such that the impeller contacts the fluid and the biological sample in the chamber.

A method of obtaining biological material may be summarized as including introducing plurality of samples containing the biological material into a respective plurality of chambers, the plurality of chambers spaced apart from each other in an array along at least a first dimension; and simultaneously agitating the samples in each of the plurality of the chambers via a plurality of agitator devices, each of the plurality of agitator devices positioned at least partially within respective ones of the plurality of chambers.

The method may further include positioning each of the plurality of agitator devices at least partially within respective ones of the plurality of chambers.

A method to agitate a plurality of biological samples may be summarized as including placing each of the plurality of biological samples in respective ones of a plurality of chambers, the plurality of chambers spaced apart from each other in an array along at least a first dimension, and each of the plurality of chambers comprising: at least a first opening to provide fluid communication with the chamber and to receive the biological sample; and an agitator device in fluid contact with the biological sample, the agitator device including a micromotor which provides rotational motion to a shaft extending from an interior of the micromotor, and an impeller fixed to the shaft such that the impeller and the shaft rotate together upon provision of the rotational motion by the micromotor; and applying electrical energy to each of the micromotors with an electrical energy source electrically coupled to the micromotors, the electrical energy sufficient to rotate the shaft and the impeller in a manner sufficient to agitate the biological samples disposed in the plurality of chambers.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not necessarily drawn to scale, and some of these elements may be arbitrarily enlarged and positioned to improve drawing legibility. Further, the particular shapes of the elements as drawn, are not necessarily intended to convey any information regarding the actual shape of the particular elements, and may have been solely selected for ease of recognition in the drawings.

FIG. 2F is a front elevational view of the array of closed tubes of FIG. 2A, according to one illustrated implementation.

FIG. 3B is a sectional elevational view of the array of closed tubes of FIG. 3A, according to one illustrated implementation.

DETAILED DESCRIPTION

Figure 1A:
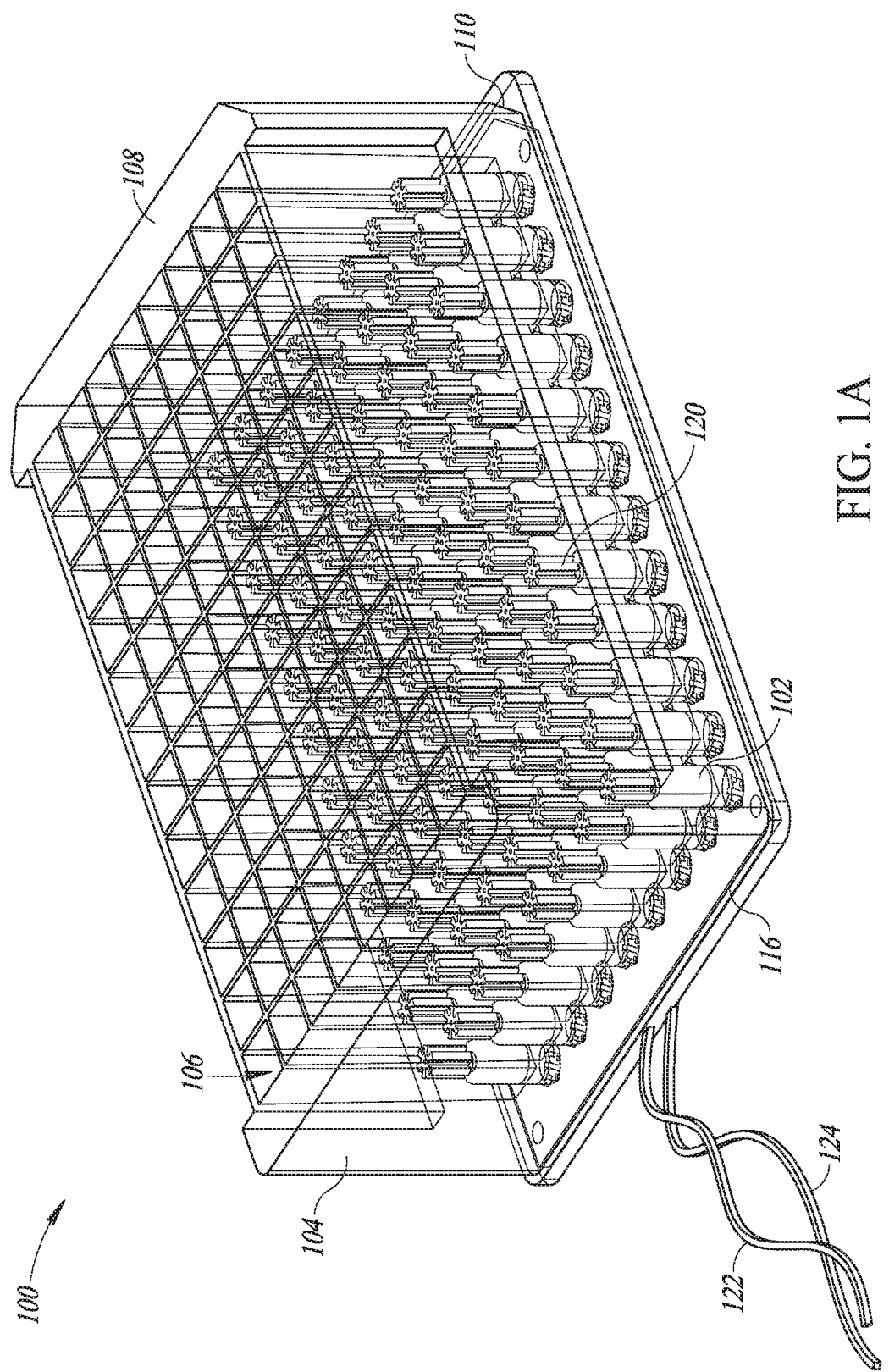
FIG. 1A is a front left isometric view of a 96 well, deep-well microtiter plate system with motors mounted from the bottom thereof for tissue homogenization and cell lysis, according to one illustrated implementation.

In the following description, certain specific details are set forth in order to provide a thorough understanding of various disclosed implementations. However, one skilled in the relevant art will recognize that implementations may be practiced without one or more of these specific details, or with other methods, components, materials, etc. In other instances, well-known structures associated with computer systems, server computers, and/or communications networks have not been shown or described in detail to avoid unnecessarily obscuring descriptions of the implementations.

Unless the context requires otherwise, throughout the specification and claims that follow, the word "comprising" is synonymous with "including," and is inclusive or open-ended (i.e., does not exclude additional, unrecited elements or method acts).

Reference throughout this specification to "one implementation" or "an implementation" means that a particular feature, structure or characteristic described in connection with the implementation is included in at least one implementation. Thus, the appearances of the phrases "in one implementation" or "in an implementation" in various places throughout this specification are not necessarily all referring to the same implementation. Furthermore, the particular features, structures, or characteristics may be combined in any suitable manner in one or more implementations.

As used in this specification and the appended claims, the singular forms "a," "an," and "the" include plural referents unless the context clearly dictates otherwise. It should also be noted that the term "or" is generally employed in its sense including "and/or" unless the context clearly dictates otherwise.

The headings and Abstract of the Disclosure provided herein are for convenience only and do not interpret the scope or meaning of the implementations.

One or more implementations of the present disclosure provide systems and methods useful for the processing of tissues and for the generation of a plurality of cells, a plurality of cell aggregates and/or tissue fragments, for example. Tissues processed according to one or more of the implementations of present disclosure can be used in various assay systems, including, but not limited to, drug validation assays, drug screening assays, proliferation assays, metabolic assays, metastasis assays, angiogenesis assays, binding assays, biochemical assays, cellular assays, genetic assays, and the like.

In particular, one or more implementations of the present disclosure provide a system with a plurality of chambers or wells which are each sized and dimensioned to receive a sample therein. The plurality of chambers may be arranged in a one dimensional or two dimensional array with uniform center-to-center spacing, in one or two dimensions, which advantageously allows for automated processing. An agitator device may be fixedly or removably positionable in one end of each of the chambers to agitate the samples disposed within each of the plurality of chambers. In at least some implementations, the agitator device may be a motor that is small in diameter (e.g., smaller than the spacing between chambers), sometimes referred to herein as a micromotor, and which is fitted with an impeller on a shaft of the micromotor.

As discussed further below, in at least some implementations, the arrayed chambers may be spaced apart in at least one dimension by a distance which extends between the centers of adjacent chamber. The distance may be any suitable standardized or customized value, such as 4.5 millimeters (mm), 6 mm, 6.35 mm, 9 mm, 10 mm, 12 mm, 12.7 mm, 13 mm, 13.5 mm, 16 mm, 18 mm, etc.

For each of the plurality of chambers, the agitator device (e.g., micromotor) may be fixedly or removably positionable at the top or bottom of the chamber. In implementations wherein the agitator device comprises a motor with an impeller, the motor may be positioned at either the top or bottom of the chamber with the impeller extending at least partially into the chamber to agitate the sample (and fluid) disposed therein.

In at least some implementations, the system may include a plurality of chambers in a standard microtiter plate format (e.g., 24 well format, 48 well format, 96 well format, or 384 well format), with the wells arranged in a one dimensional or two dimensional uniform array. In at least some implementations, the system may include a plurality of individual tubes arranged with close, uniform spacing. Such uniform arrays of chambers may allow for efficient, automated processing of samples.

In operation, one or more voltage sources may be operatively coupled to each of the motors to cause the impellers positioned in each of the plurality of chambers to be rotatably driven to perform numerous activities, including, but not limited to, cell lysis in the presence of particular lysis material/beads, tissue disruption and homogenization with or without the presence of particular lysis material, tissue disaggregation (i.e., intact single-cell generation) without particulate lysis material, and nucleic acid extraction using particulate material. Each of the chambers may become a closed system after the sample is added and either the agitator device (e.g., motor) is inserted into an opening or a cover (e.g., cap, film) is used to close each of the chambers during the agitation process. Additionally or alternatively, in implementations wherein the agitator devices are positioned at the bottom of each of the chambers, the top of each of the chambers may be left open during processing.

In at least some implementations, the systems and methods described herein use novel devices which incorporate micromotors to provide mechanical energy to fluids containing tissue specimens or samples. Such micromotors may be similar or identical to those employed in cell phones to provide vibration of the phone, for example. Such micromotors are also commonly employed in toys and robotic devices, for example, in model helicopters and model boats. In at least some implementations, the micromotors may be operated by application of a direct current (DC) voltage to the terminals of the micromotors. Most applications of the micromotors are for battery powered devices and the micromotors are, therefore, generally designed to operate at a voltage of 1.5 volts or greater. The micromotors may be generally cylindrical in shape and may have a diameter of less than 15 millimeters (mm), for example. Because the micromotors are small, they generally do not deliver very much torque, but may rotate at very high rate. For some micromotors, rotation of up to 50,000 revolutions per minute (rpm) or greater are possible. The rotation speed of the micromotors is generally dependent on the voltage applied. Most applications, however, use the micromotors at the upper end of their speed rating and, thus, at the upper end of their recommended voltage specification. Because the motors are designed and manufactured to operate at high rotational speeds, they typically provide only low torque. As a consequence, the motors may not begin to turn if the shaft extending from the cylindrical body is in contact with another object. Similarly, the motors stop turning easily if the shaft makes contact with another object.

Because of the low torque nature of micromotors, for many applications there can be no significant seal mechanism around the shaft to keep fluids from entering the body of the motor. Encircling the shaft with a fluid barrier such as a grommet or O-ring may result in significantly reduced speeds, or more commonly, inability to turn on the motor to rotate.

In some implementations of the present disclosure, the motors are used in direct contact with the fluid and/or tissue specimen, hence, without any fluid barrier to impede the rotation of the shaft and impeller. This configuration allows the motor to operate at high RPMs to drive the shaft and impeller at high speed. In one or more implementations of the present disclosure, the shaft and metal of the motor are treated with a silane compound such as HMDS (hexamethyldisilizane) or alkylsilane. As understood by those skilled in the art, such treatment causes a reaction between the silane and the metal surface to form a very thin layer on the surface of the metal. In general, it was found that treatment with hydrophobic silanes such as HMDS or alkylsilane impedes the penetration of fluid into the motor body and thus improves the performance of the motor in direct contact with the fluid. The silane treatment may form a hydrophobic barrier and the high surface tension of water does not allow it to pass the narrow passage between the shaft and the motor body.

In at least some implementations, the system includes a plurality of uniformly spaced chambers or wells, such as a microtiter plate or a plurality of micro-centrifuge tubes arranged in a support rack which provides uniform spacing. Each of the chambers receives at least a portion of an agitator device therein. The agitator device may be sized and dimensioned so that a portion thereof can be inserted into an opening of the chamber and may comprise a micromotor having a shaft at one end and an impeller fitted on the end of the shaft. The micromotor can be connected to a voltage or current source to drive the micromotor.

Figure 1B:
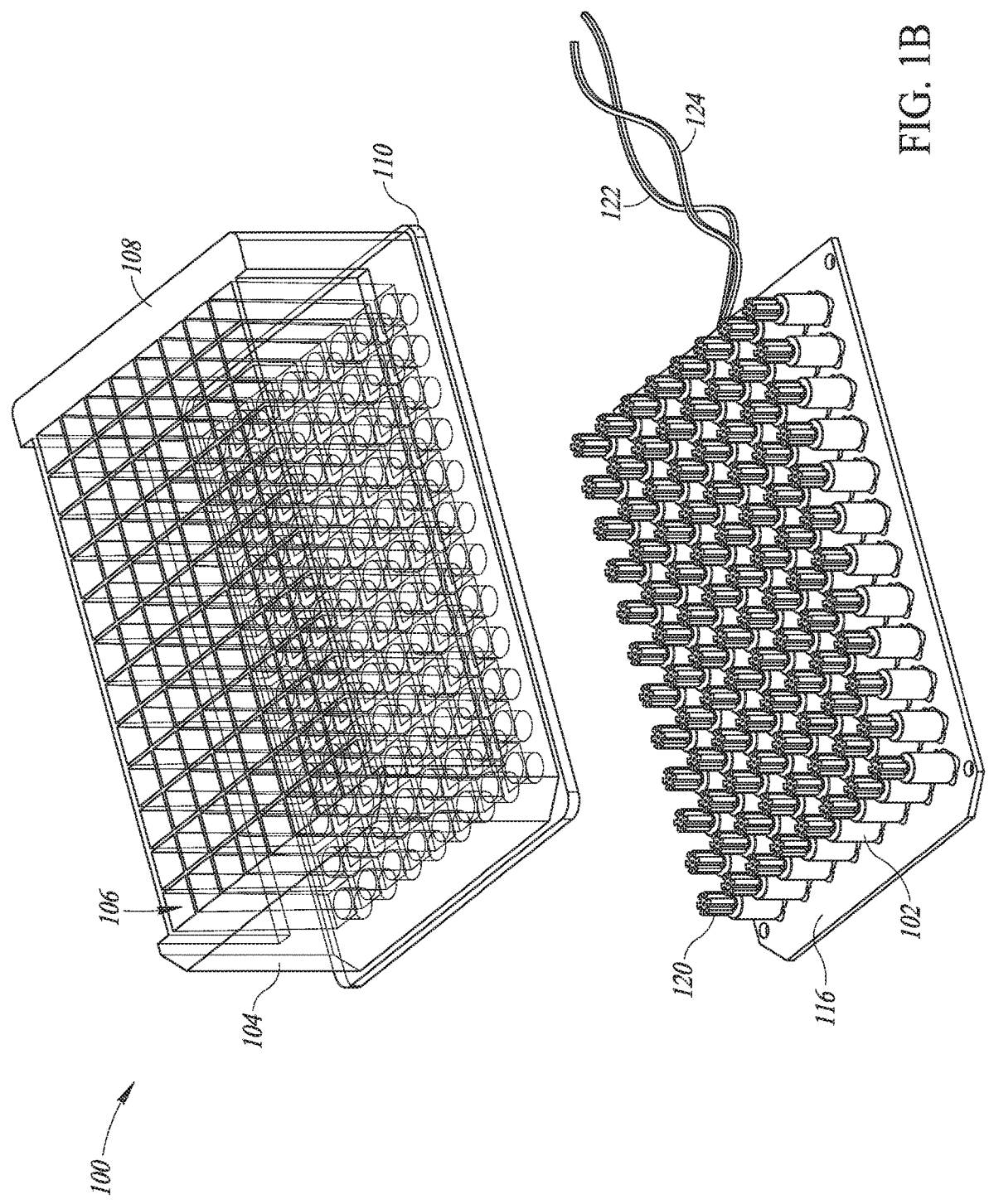
FIG. 1B is an isometric view of the microtiter plate system of FIG. 1A with a motor assembly of the microtiter plate system removed from a well assembly, the well assembly made transparent to show various portions of the system, according to one illustrated implementation.

FIGS. 1A-1F show various views of a 96 well, deep-well microtiter plate system 100 with motors 102 mounted from the bottom thereof for tissue homogenization (e.g., without particulate or beads) and cell lysis (e.g., with particulate or beads). As shown in FIG. 1B, the system 100 includes a well assembly or body portion 104 which includes a plurality of openings 106 that extend between a top end 108 and a bottom end 110 of the body portion 104. In this illustrated implementation, the body portion 104 includes 96 openings 106 uniformly spaced in an 8×12 array. Each of the openings 106 defines a chamber having a top opening 112 (FIG. 1C) at the top end 108 of the body portion 104 and a bottom opening 114 (FIG. 1C) at the bottom end 110 of the body portion 104. In other implementations, the system 100 may include more or less chambers. For example, in at least some implementations the body portion 104 may conform to other standard plate formats, such as a 6 well format, a 24 well format, a 48 well format, a 384 well format, etc.

The system 100 also includes a motor plate or carrier 116 which carries the 96 micromotors 102 thereon. Each of the micromotors 102 is aligned with and corresponds to a different one of the plurality of openings 106 in the body portion 104 of the system 100. Each micromotor 102 includes a shaft 118 (see FIGS. 1C and 1E) that protrudes upward from the micromotor and an impeller 120 is attached to the shaft. Wire leads 122 and 124 (FIG. 1A) are attached to the motor carrier 116 to allow the motor carrier to receive power from a power source (e.g., battery, AC mains, AC/DC converter) coupled to the leads. For example, the motor carrier 116 may include circuitry (not shown) which receives power via the leads 122 and 124, and distributes the power to each of the micromotors 102 to cause the impellers 120 to be rotatably driven. The circuitry may include various components (e.g., converters, filters, logic) which operate to condition power received via the leads 122 and 124 to be suitable to be supplied to each of the micromotors 102.

In at least some implementations, one lead 122 is designated as negative and the other lead 124 is designated positive. When attached to a battery or other power source having negative and positive terminals attached to the negative wire lead 122 and positive wire lead 124, respectively, the motor shafts 118 and impellers 120 of the motors 102 will rotate in, for example a clockwise direction. If the two wire leads 122 and 124 are reversed, the rotation of the shafts and impellers will be counter-clockwise. Application of a voltage waveform such as a sine wave, triangle wave, square wave, or more complex waveforms will result in changes in the rotation speed and direction of the shafts and impellers.

Figure 1C:
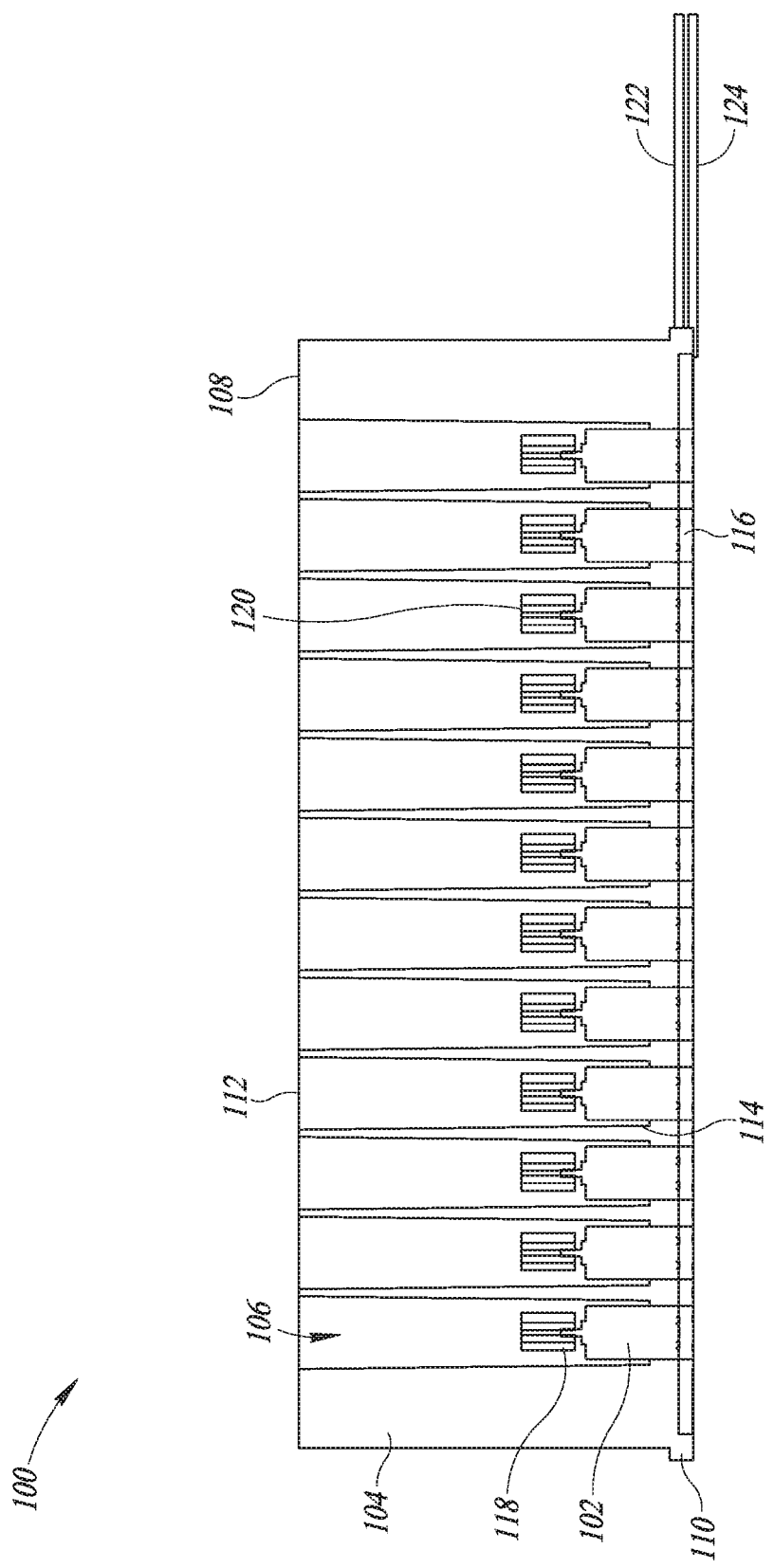
FIG. 1C is a sectional elevational view of the microtiter plate system of FIG. 1A, according to one illustrated implementation.
Figure 1D:
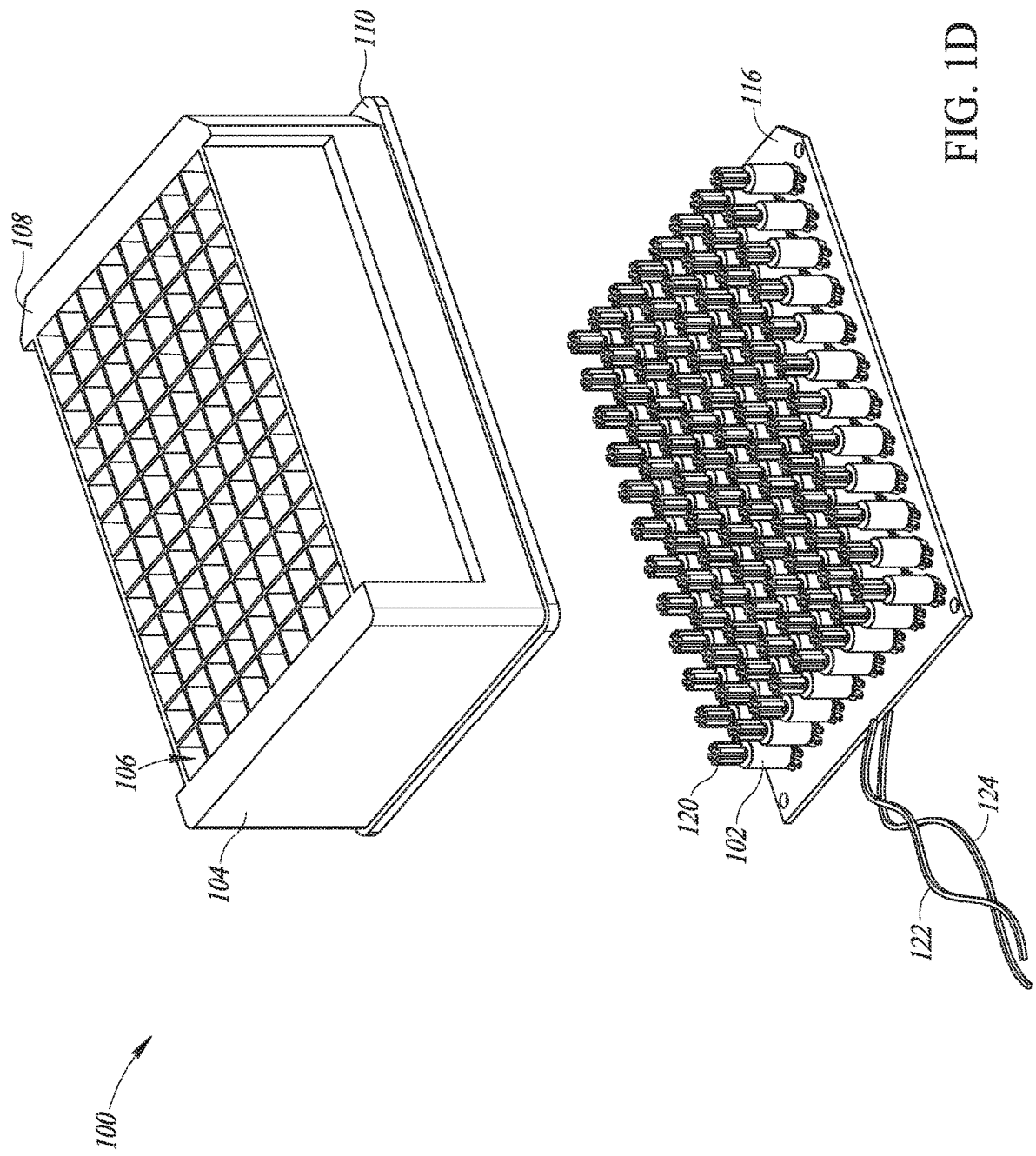
FIG. 1D is an isometric view of the microtiter plate system of FIG. 1A with the motor assembly removed from the well assembly, according to one illustrated implementation.
Figure 1E:
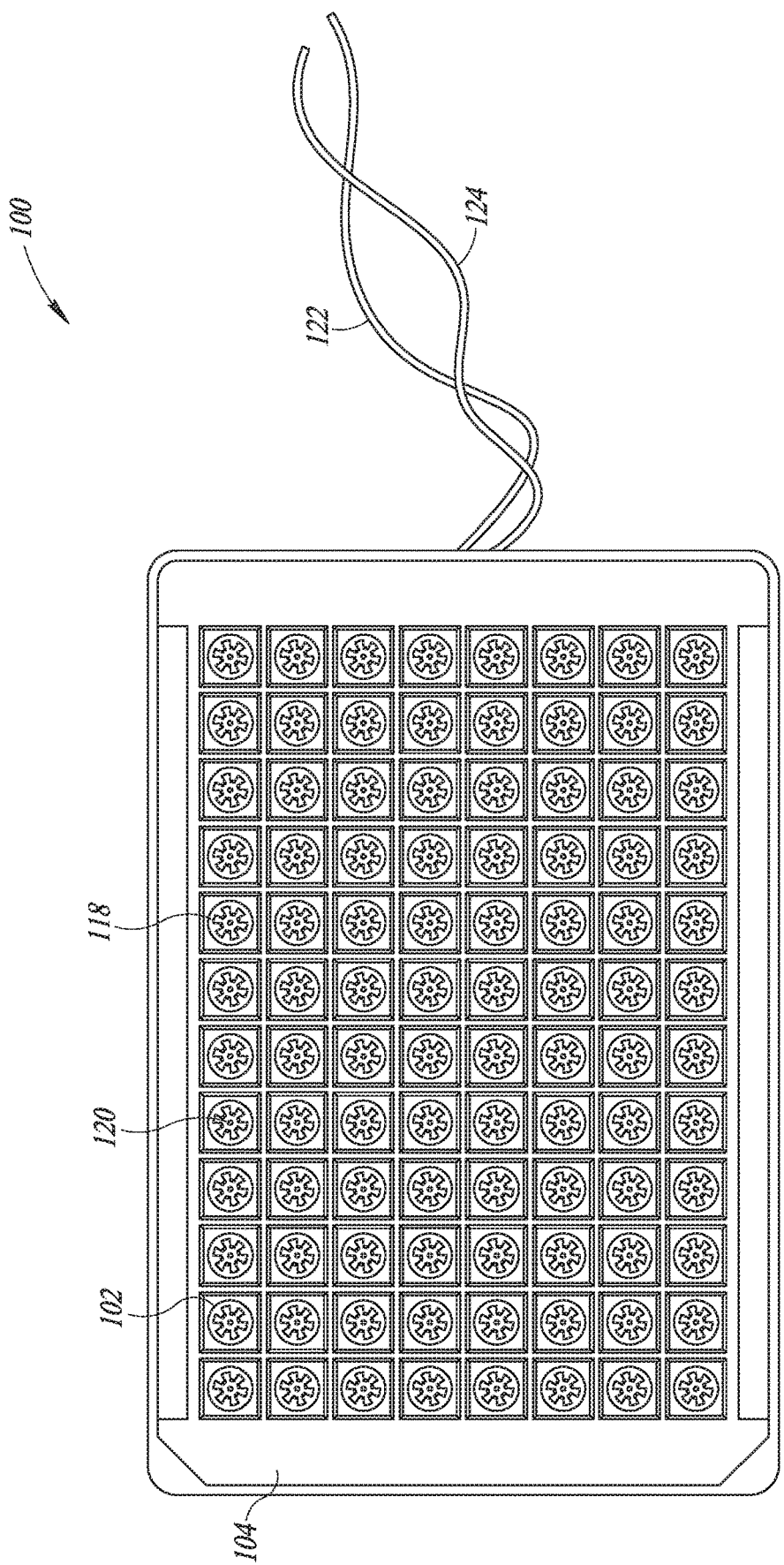
FIG. 1E is a top plan view of the microtiter plate system of FIG. 1A, according to one illustrated implementation.
Figure 1F:
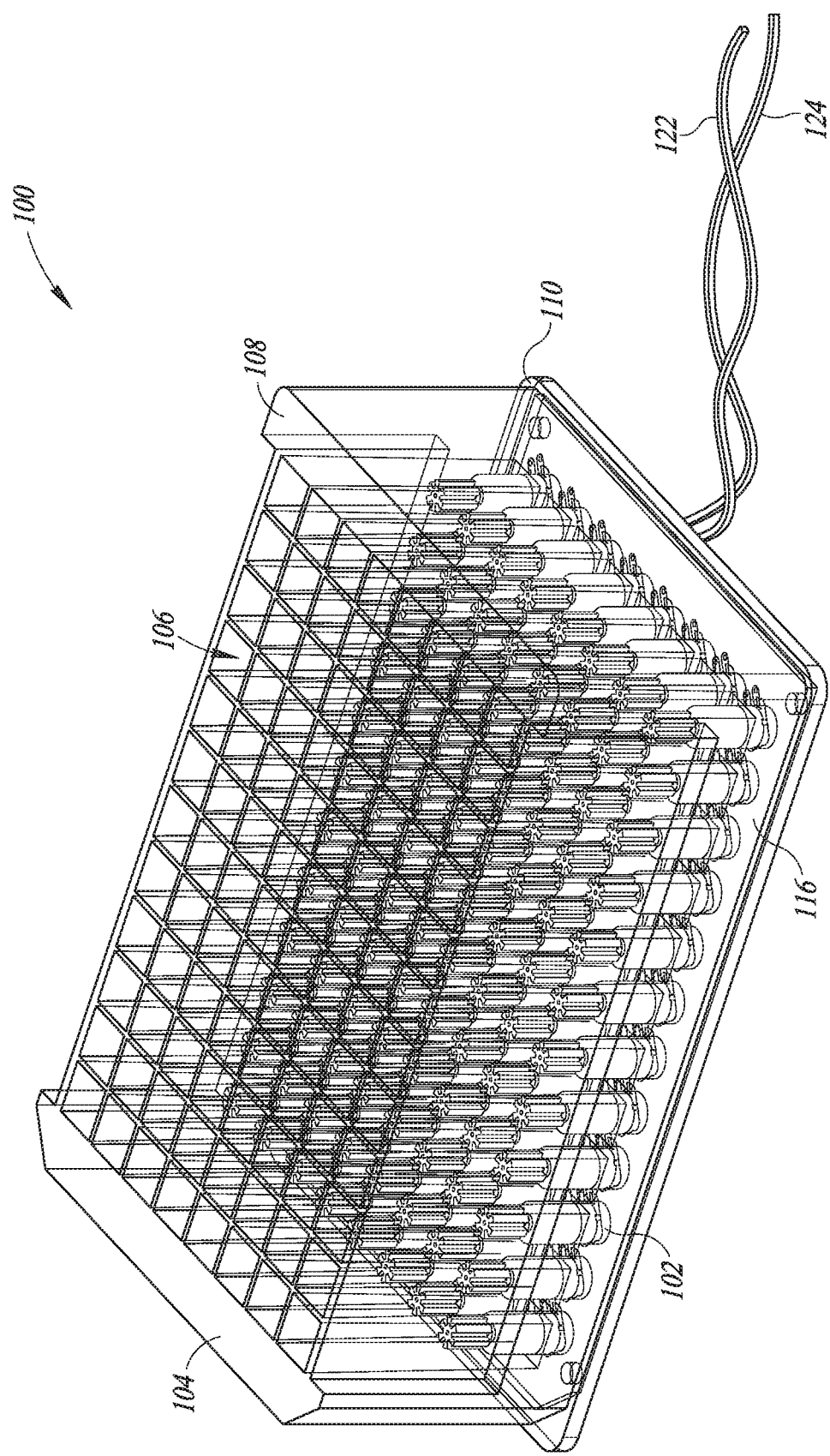
FIG. 1F is a front right isometric view of the microtiter plate system of FIG. 1A, according to one illustrated implementation.

As shown in FIGS. 1A and 1C, when the body portion 104 is placed onto the motor carrier 116, each of the openings 106 surrounds one of the micromotors 102 and impellers 120. As discussed above, the micromotors 102 may be of the types that are commonly used in cell phones to provide vibration alerts to the user. In at least some implementations, the micromotors 102 may be 4 mm to 7 mm in diameter but can have other diameters (e.g., 3 mm, 10 mm, 20 mm) for example. Such micromotors work surprisingly well in the applications of the present disclosure because they are small enough to fit into standard microcentrifuge tubes and/or individual wells of microtiter plates. Further, the micromotors are able to operate at a high speed (e.g., 20,000 to 50,000 rpm) in direct contact with fluid for a length of time sufficient to perform agitation of biological samples. The micromotors are also advantageous in that they can be operated using batteries as the voltage source since they draw only, for example, 20 to 100 mA of current each. Further, the micromotors are inexpensive enough that the entire apparatus can be disposable after a single use or after multiple uses.

The systems of the present disclosure, in many implementations, use micromotors which are sealed with a plastic material or other material at the end opposite the shaft end of the micromotor. It was discovered that sealing the end of the micromotor facilitates operation of the micromotor in direct contact with the fluid which contains the tissue. With the non-shaft end of the motor sealed, the only opening to the interior of the micromotor is around the shaft of the motor. Sealing of the opposite end presumably helps to keep fluid from flowing into the interior of the micromotor which could ultimately cause electrical failure. In a test, it was shown that sealed micromotors can function for several hours in contact with saline whereas non-sealed micromotors only operated for a few minutes.

In the illustrated implementation, each chamber includes the top opening 112 for the introduction of a sample and fluid and the bottom opening 114 in which one of the micromotors 102 is sealingly engaged. Since the micromotors 102 in this implementation are positioned within the bottom openings 114 of the chambers, gravity will pull the samples and fluid into contact with the impellers 120 of the micromotors 102. The motor carrier 116 supports the opposite ends of the micromotors 102. Although not shown, a cover (e.g., lid, film) may optionally be fitted onto the top openings 114 of the chambers during the agitation process so the fluid and samples remain in the chambers.

To perform agitation, samples are placed into each of the chambers, generally with a fluid such as saline that is compatible with the samples. At least a portion of the micromotor 102 in each chamber is exposed to the fluid and samples during operation. Power is then applied to each of the micromotors 102 such that the motor shafts 118 and impellers 120 turn, which causes simultaneous mechanical agitation of each of the samples in each of the chambers of the system 100. Following agitation, the fluid and samples in each of the chambers may be manually or autonomously removed, for example with a syringe or pipettor, and the samples can be transferred other containers for analysis.

In some implementations, particulate material may be added to each of the chambers. Such particulate material, e.g., ceramic or glass beads, may aid in the mechanical agitation of the tissue samples. The particulate material may take a variety of forms. While often referred to herein as beads, the term bead is not meant to be limiting with respect to size or shape. The particulate material may, for example, comprise ceramic, glass, zirconia, zirconia/silica, zirconium silicate, metal, plastic, nickel, tungsten, tungsten carbide, yttrium stabilized zirconia, sand, and/or particles of any geometry such as shard or of random shape.

In implementations that utilize particulate material, the size of the beads may be 0.03 mm or less, 0.05 mm, 0.08 mm, 0.1 mm, 0.2 mm, 0.3 mm, 0.4 mm, 0.5 mm, 0.65 mm, 0.8 mm, or 1 mm or above. The optimal size for many applications, especially for hard-to-lysis bacteria, may be approximately 0.1 mm (e.g., 0.1 mm+/−0.015 mm), for example. In at least some implementations, the size range of 0.08 mm to 0.2 mm is very useful. Larger microorganisms (e.g., yeast, oocysts) and some tissue (e.g., plant or tough animal tissue) will sometimes benefit for a larger bead size ranges of 0.2 mm and above.

The amount of beads used in a chamber may depend on the size of chamber and volume of liquid in the well. In at least some implementations, the volume of beads used in each chamber may be 0.04-0.06 mL, 0.06-0.09 mL, 0.09-0.12 mL, as well as greater than 0.12 mL and in some cases much greater (e.g., up to 0.35 mL to 0.5 mL of bead volume). For example, the system 100 (with about 2 mL volume chambers, for example), and other systems disclosed herein, may operate optimally for a 1 mL liquid sample of bacteria using a volume of lysing material that is 0.4 mL+/−0.05 mL.

In at least some implementations, the motors may be operated at 7,000 rpm or below, 7,000 to 11,000 rpm, 11,000 to 20,000 rpm, 20,000 to 27,000 rpm, 27,000 to 35,000 rpm, or 35,000 rpm and greater. For some particular motors, the above-listed speeds are obtained using voltages of 1 V or less, 1.5 V, 3 V, 4.5 V, 6 V, and 6.5 V and greater, respectively.

Figure 2A:
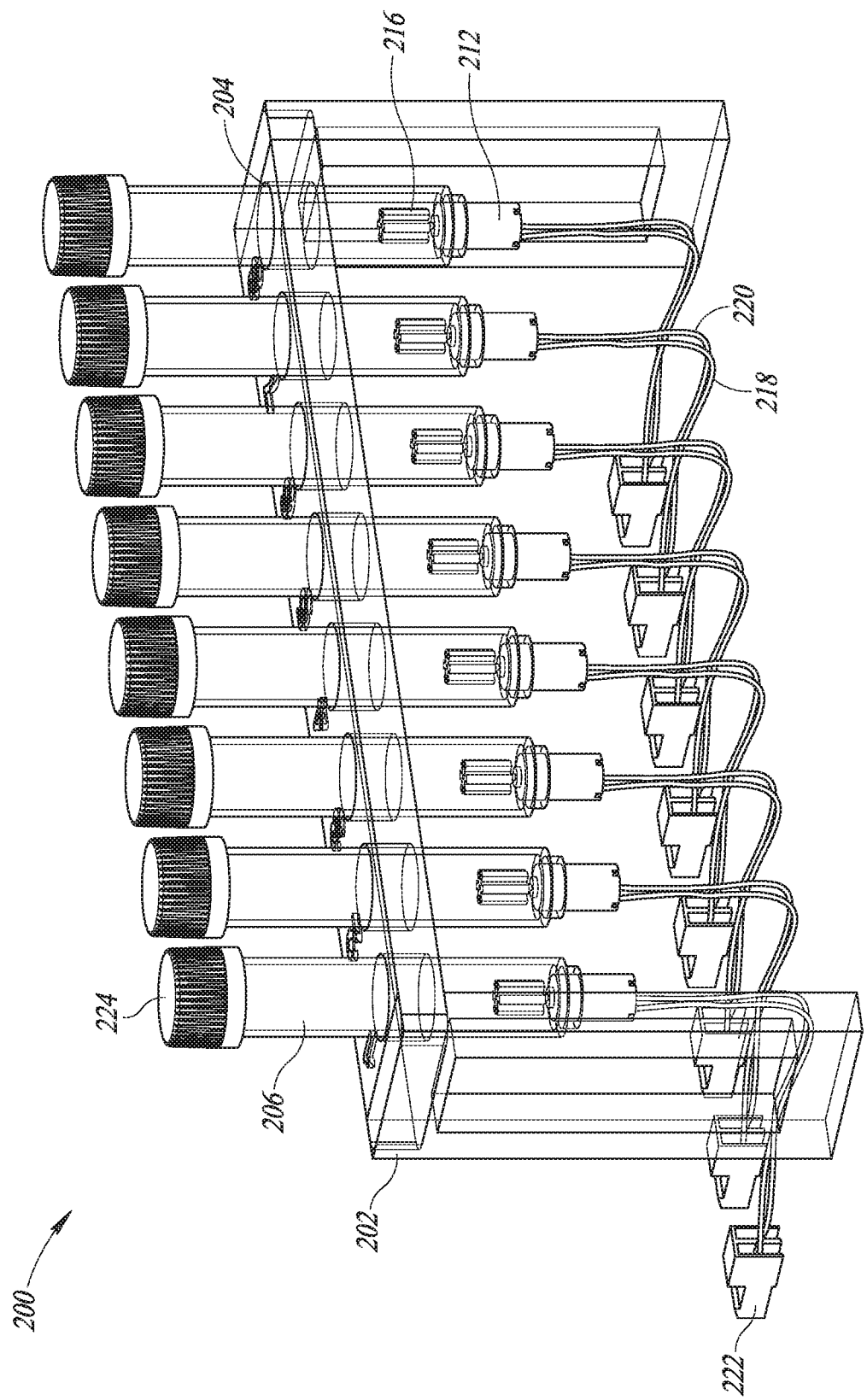
FIG. 2A is a front right isometric view of an equally spaced array of closed tubes with motors mounted from the bottom thereof for tissue homogenization and cell lysis, according to one illustrated implementation.
Figure 2B:
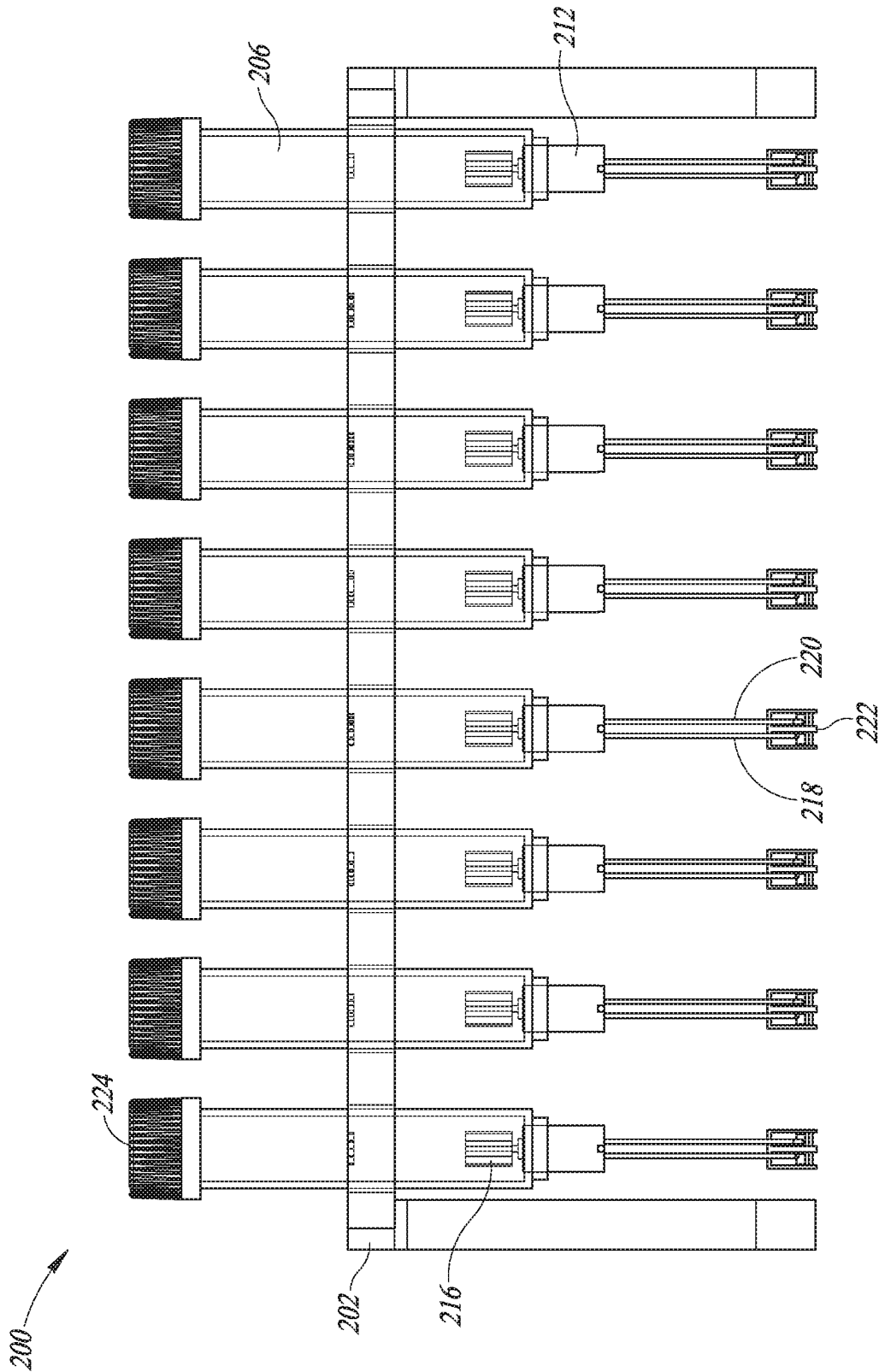
FIG. 2B is front elevational view of the array of closed tubes of FIG. 2A, according to one illustrated implementation.
Figure 2C:
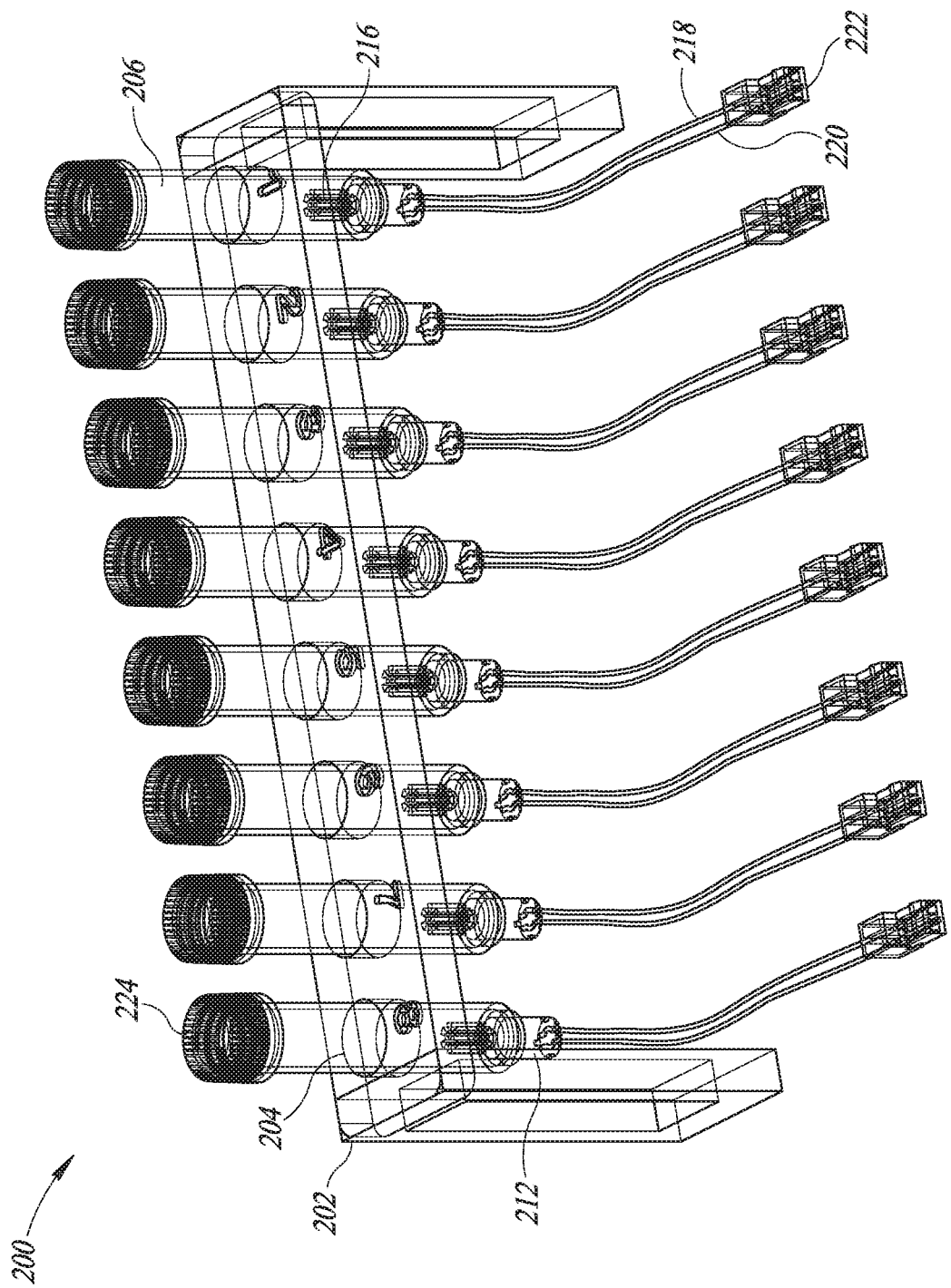
FIG. 2C is a rear left isometric view of the array of closed tubes of FIG. 2A, according to one illustrated implementation.
Figure 2D:
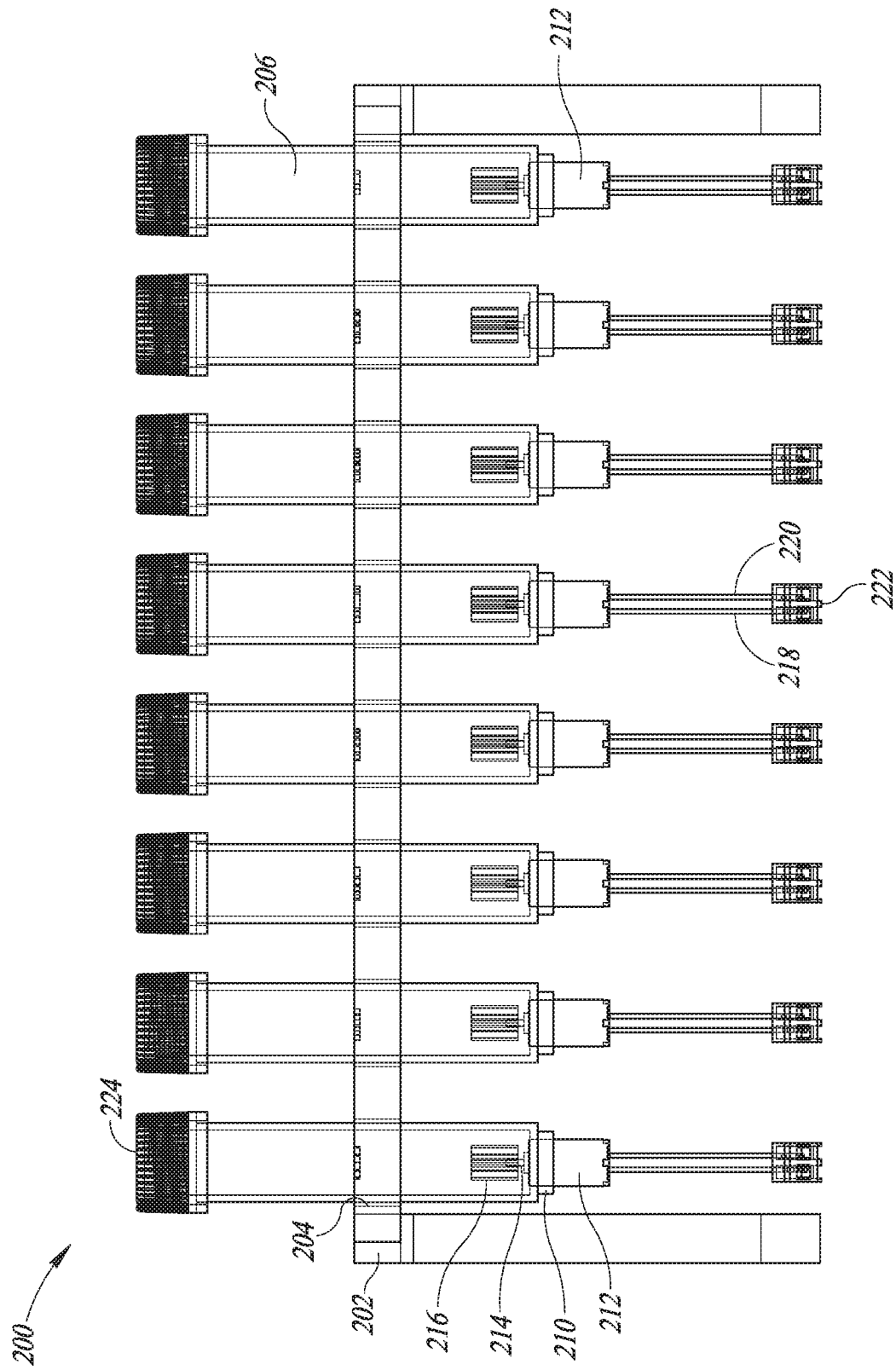
FIG. 2D is a rear elevational view of the array of closed tubes of FIG. 2A, according to one illustrated implementation.
Figure 2E:
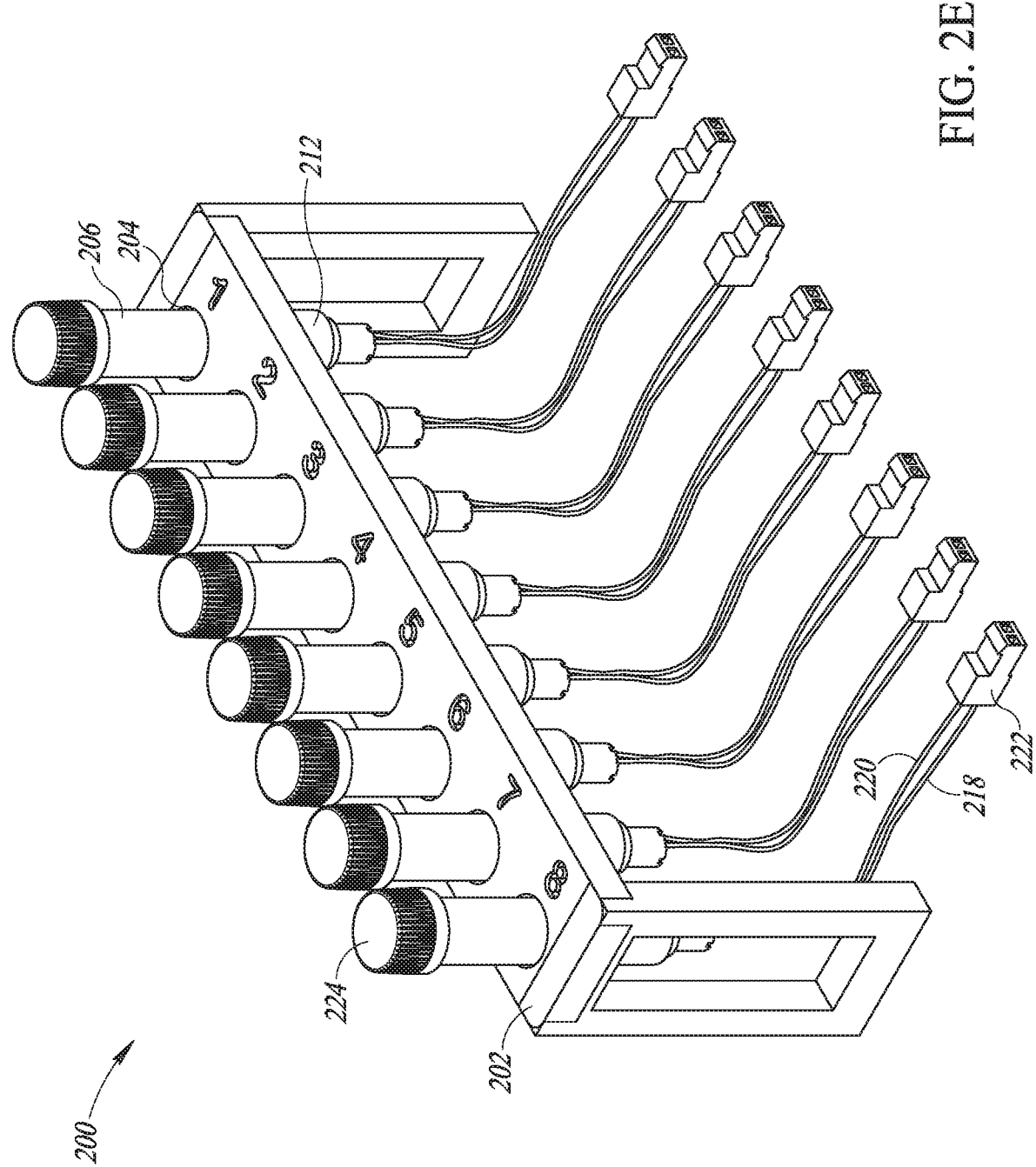
FIG. 2E is a rear left isometric view of the array of closed tubes of FIG. 2A, according to one illustrated implementation.
Figure 2G:
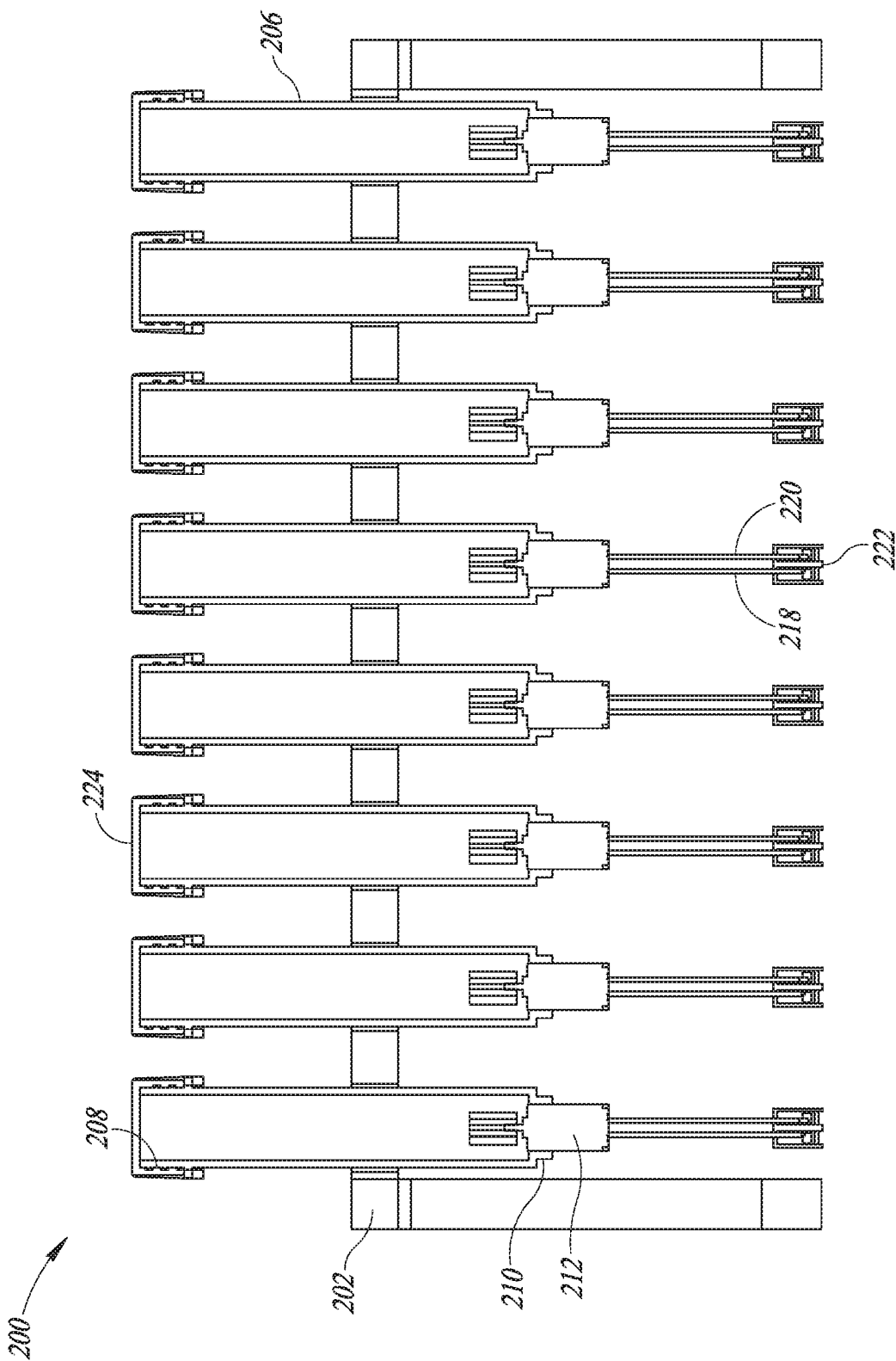
FIG. 2G is a sectional elevational view of the array of closed tubes of FIG. 2A, according to one illustrated implementation.
Figure 3A:
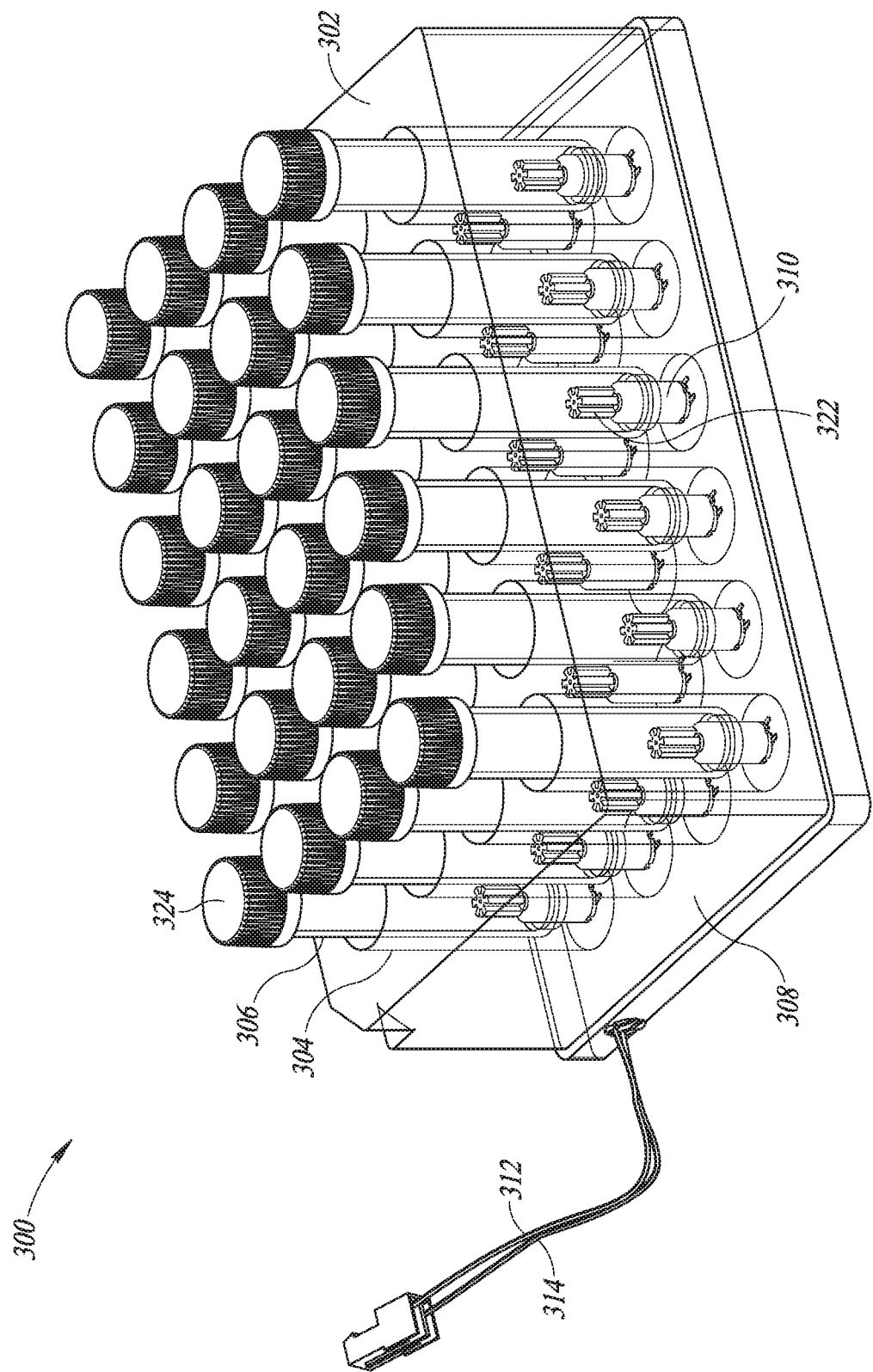
FIG. 3A is a front left isometric view of a two dimensional array of closed tubes with motors mounted from the bottom in a 24 well format plate, with the plate made transparent to show various portions of the system, according to one illustrated implementation.
Figure 3C:
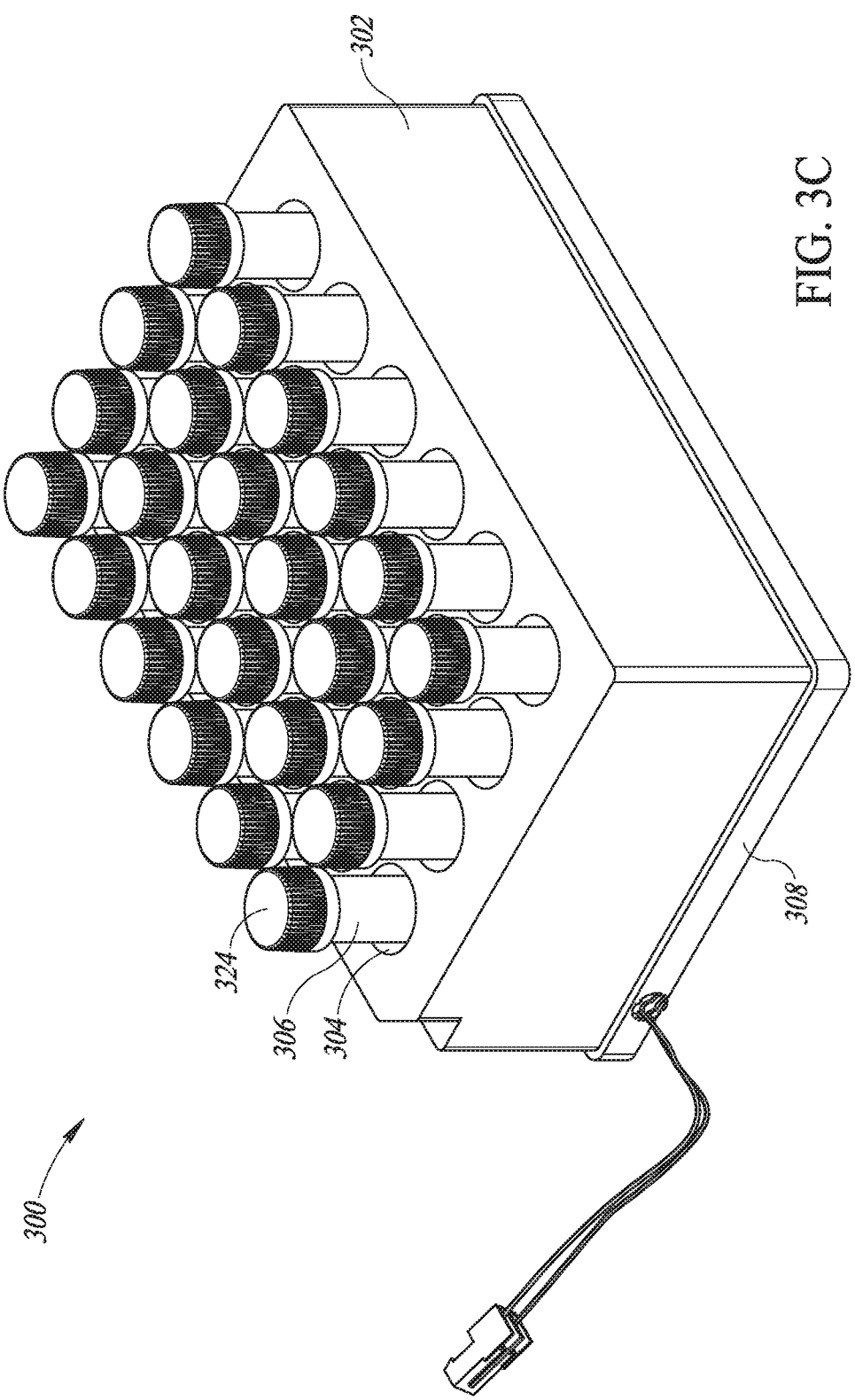
FIG. 3C is a front left isometric view of the array of closed tubes of FIG. 3A, according to one illustrated implementation.
Figure 3D:
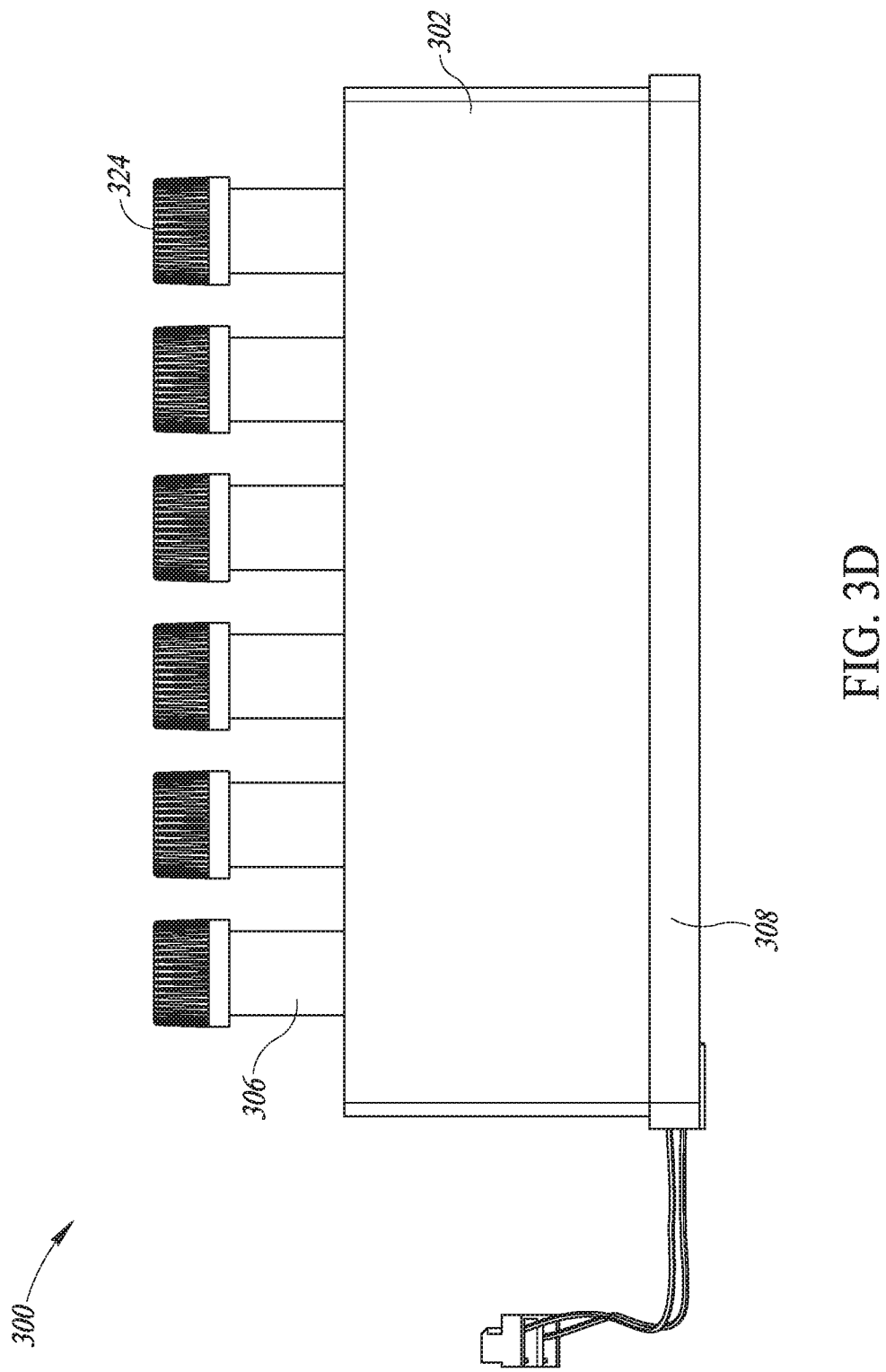
FIG. 3D is a left elevational view of the array of closed tubes of FIG. 3A, according to one illustrated implementation.

FIGS. 2A-2G show another implementation of a system 200 for tissue homogenization, cell lysis, etc. The system 200 includes a support rack 202 having a plurality of uniformly spaced openings 204 therein. In the illustrated example there are eight openings 204 but in other implementations more or less openings may be present (e.g., 4 openings, 12 openings, 48 openings). Each of the openings 204 is sized and dimensioned to receive a container 206 therein, such that when the containers are positioned in openings of the support rack 202, the containers are uniformly spaced in a linear array. The center-to-center spacing between each of the openings 202, and thus the containers 206, may be any suitable standardized or customized distance (e.g., 12 mm, 15 mm, 18 mm, 20 mm). The support rack 202 may be plastic, metal or other solid material. As shown in FIG. 2G, each of the containers 206 has a first opening 208 and a second opening 210 opposite the second opening. A micromotor 212 is sealingly engaged in the second opening 210 of each of the containers 206. Protruding from the one end of the micromotor is a shaft 214 (FIG. 2D) upon which is mounted an impeller 216. Electrically attached to the micromotor 212 are two electrical leads or wires 218 and 220. Each pair of leads 218 and 220 may be attached to a connector 222 to allow simple attachment to a voltage source (e.g., battery, power supply). Each of the first openings 208 of the containers 206 may be optionally closed with a removably and sealingly engaged cap 224 which seals the container during use to contain a fluid and tissue during the agitation process.

FIGS. 3A-3D show various views of a system 300 for tissue homogenization, cell lysis, etc. The system 300 includes a housing 302 which includes 24 uniformly spaced openings 304 arranged in a two dimensional array. Each of the openings 304 in the housing 302 receives a container 306 (e.g., tube) therein. A bottom motor carrier portion 308 has 24 micromotors 310 mounted thereon which each extend into a different one of the 24 openings from the bottom. Wire leads 312 and 314 (FIG. 3A) are attached to circuitry of the motor carrier 308 to allow the simultaneous application of a voltage or voltage waveform to each of the micromotors, as discussed above.

Each of the openings in the housing 302 is sized and dimensioned to receive one of the containers 306 therein, such that when the containers are positioned in the openings of the housing, the containers are uniformly spaced in a two dimensional array. In the illustrated example, the array is 4×6, such a standard 24 well plate, but other dimensions or formats (e.g., 48 well format, 96 well format) may be used in other implementations. The center-to-center spacing between each of the containers 306 may be any suitable standardized or customized distance (e.g., 12 mm, 15 mm, 18 mm, 20 mm). The housing 302 may be plastic, metal or other solid material.

As shown in FIG. 3B, each of the containers has a first opening 316 and a second opening 318 opposite the second opening. One of the micromotors 310 is sealingly engaged in the second opening 318 of each of the containers 306. Protruding from the one end of the micromotor is a shaft 320 upon which is mounted an impeller 322. Each of the first openings 316 of the containers 306 may be optionally closed with a removably and sealingly engaged cap 324 which seals the container during use to contain a fluid and sample during the agitation process.

Figure 4A:
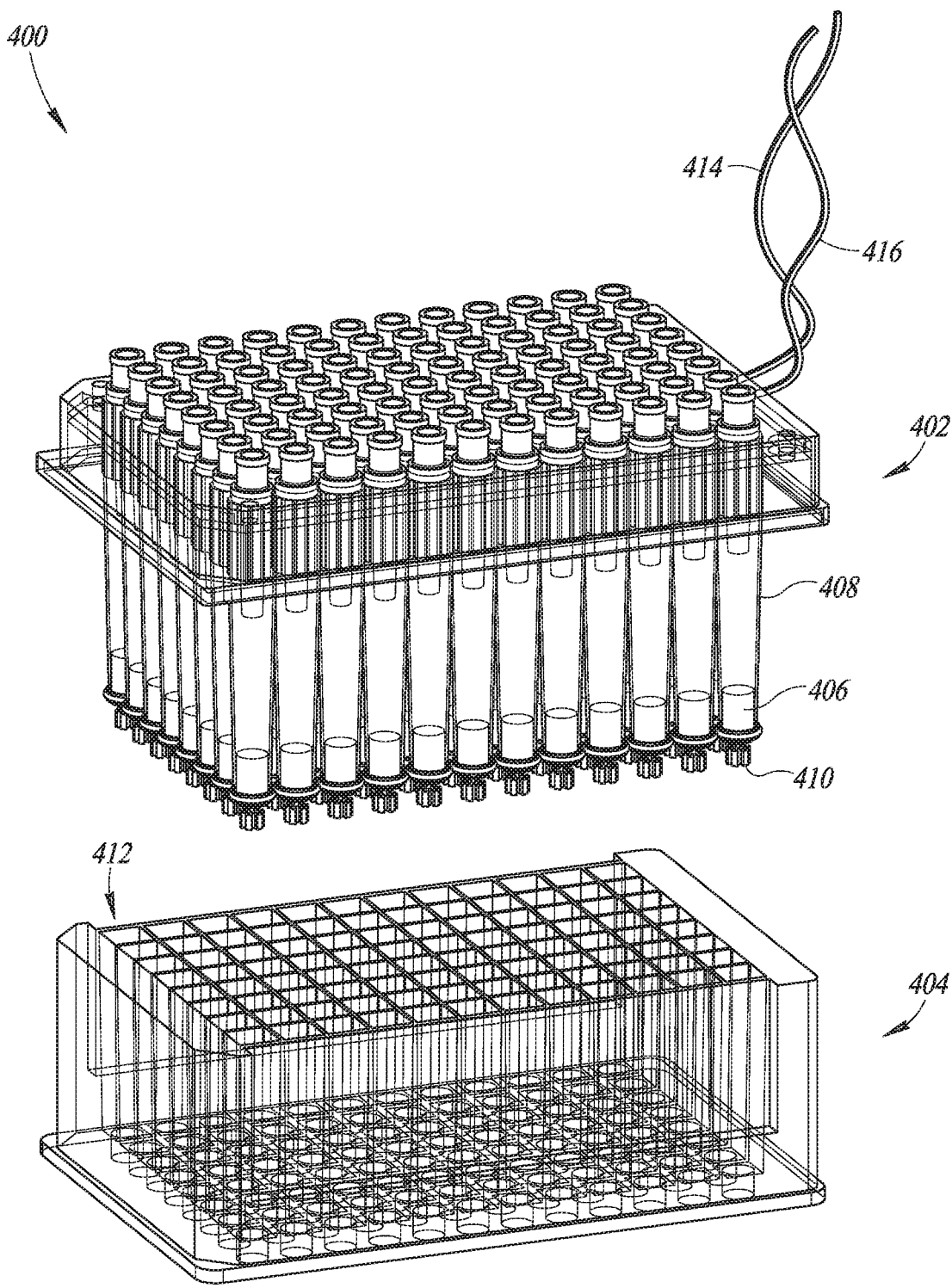
FIG. 4A is an isometric view of a spaced array of motors and a 96 well, deep-well microtiter plate, with the motors coupled to ends of an array of pipette tips of a robotic liquid handler, according to one illustrated implementation.
Figure 4B:
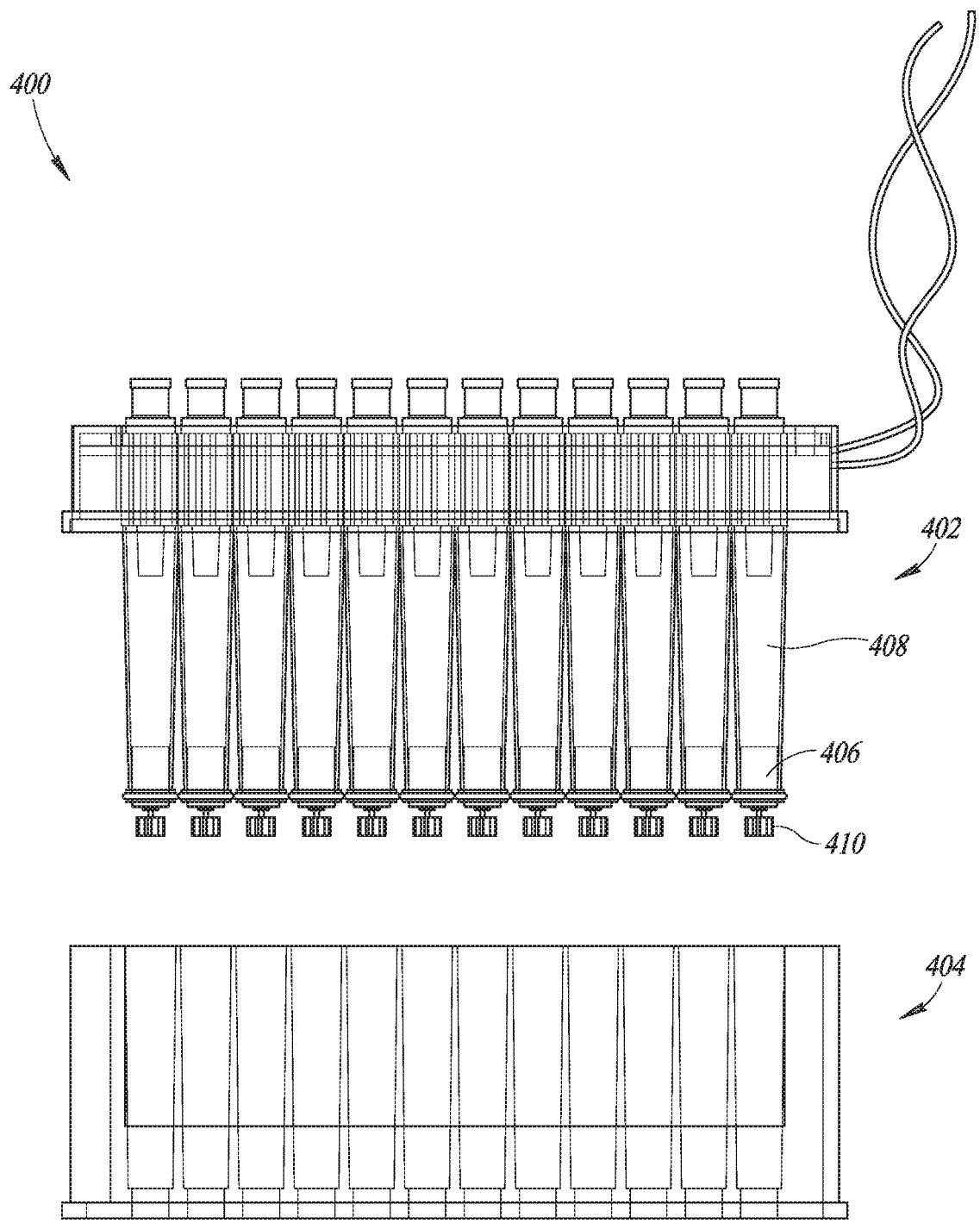
FIG. 4B is an elevational view of the motors and microtiter plate of FIG. 4A, according to one illustrated implementation.
Figure 4C:
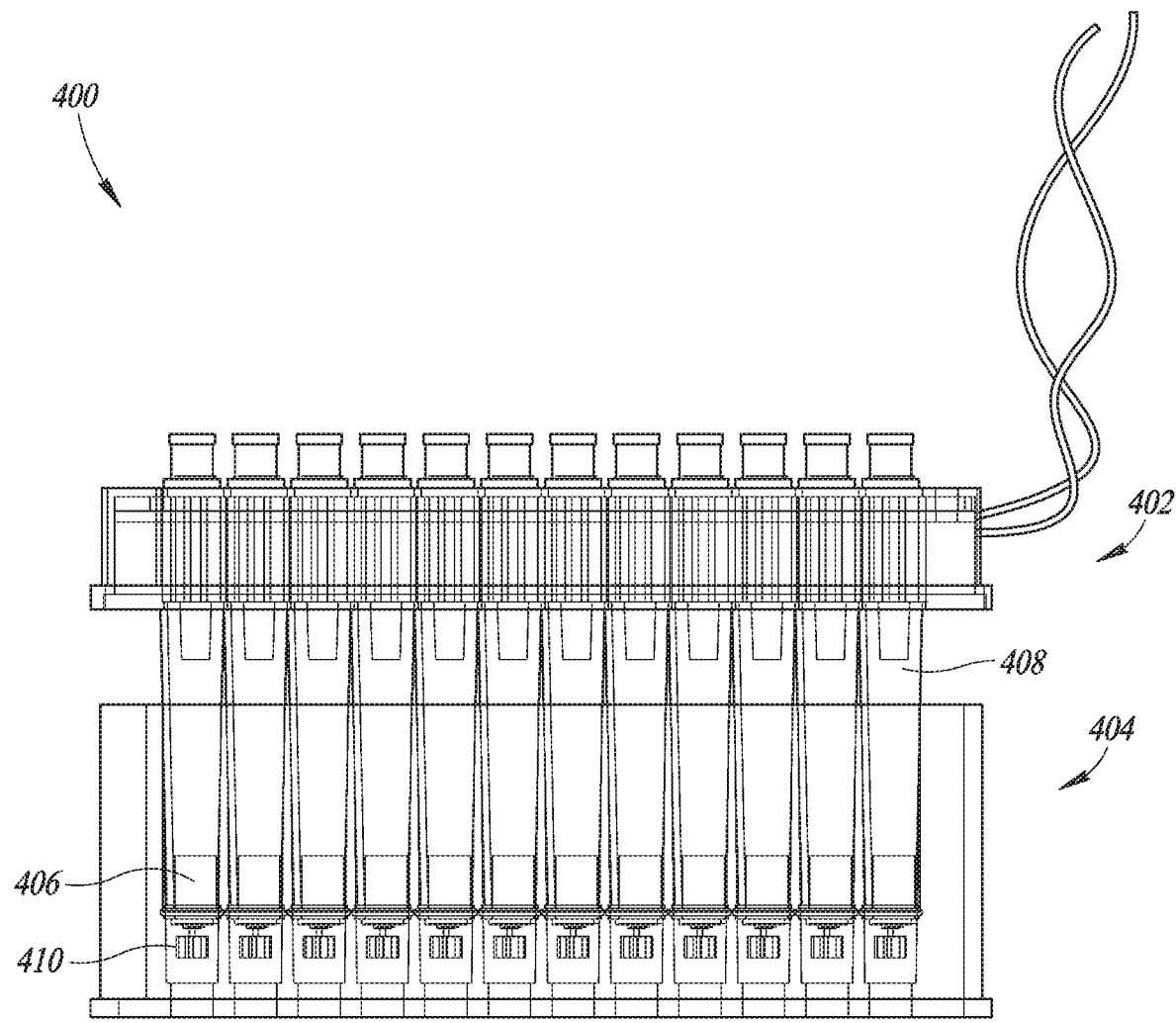
FIG. 4C is an elevational view of the motors and microtiter plate of FIG. 4A, wherein each of the individual motors are disposed in one of the wells of the microtiter plate, according to one illustrated implementation.

FIGS. 4A-4C show various views of a system 400 which includes a motor assembly 402 and a 96 well, deep-well microtiter plate 404. In this implementations, the motor assembly 402 comprises 96 motors 406 that are each coupled to lower ends of pipette tips 408 of a robotic liquid handler. Each of the motors 406 is arranged with its respective impeller 410 facing downward toward the microtiter plate 404. In operation, samples may be disposed into each of the 96 wells 412 of the microtiter plate 404. Then, as shown in FIG. 4C, the motor assembly 402 may be moved downward onto the microtiter plate 404 such that each of the motors 406 coupled to the pipette tips 408 is lowered into one of the wells 412 such that the impellers 410 of the motors are placed into contact with the fluid/samples in each of the wells. Wire leads 414 and 416 are attached to circuitry of the motor assembly 402 to allow the simultaneous application of a voltage or voltage waveform to each of the micromotors 406 so that the samples in the wells 412 may be processed, as discussed above. Although in this example a 96 well format with 9 mm spacing is used, in other implementations other formats (e.g., 6 well format, 24 well format, 48 well format, 384 well format) and/or spacings (e.g., 4.5 mm, 6 mm, 6.35 mm, 9 mm, 10 mm, 12 mm, 12.7 mm, 13 mm, 13.5 mm, 16 mm, 18 mm, etc.), may be used.

Figure 5A:
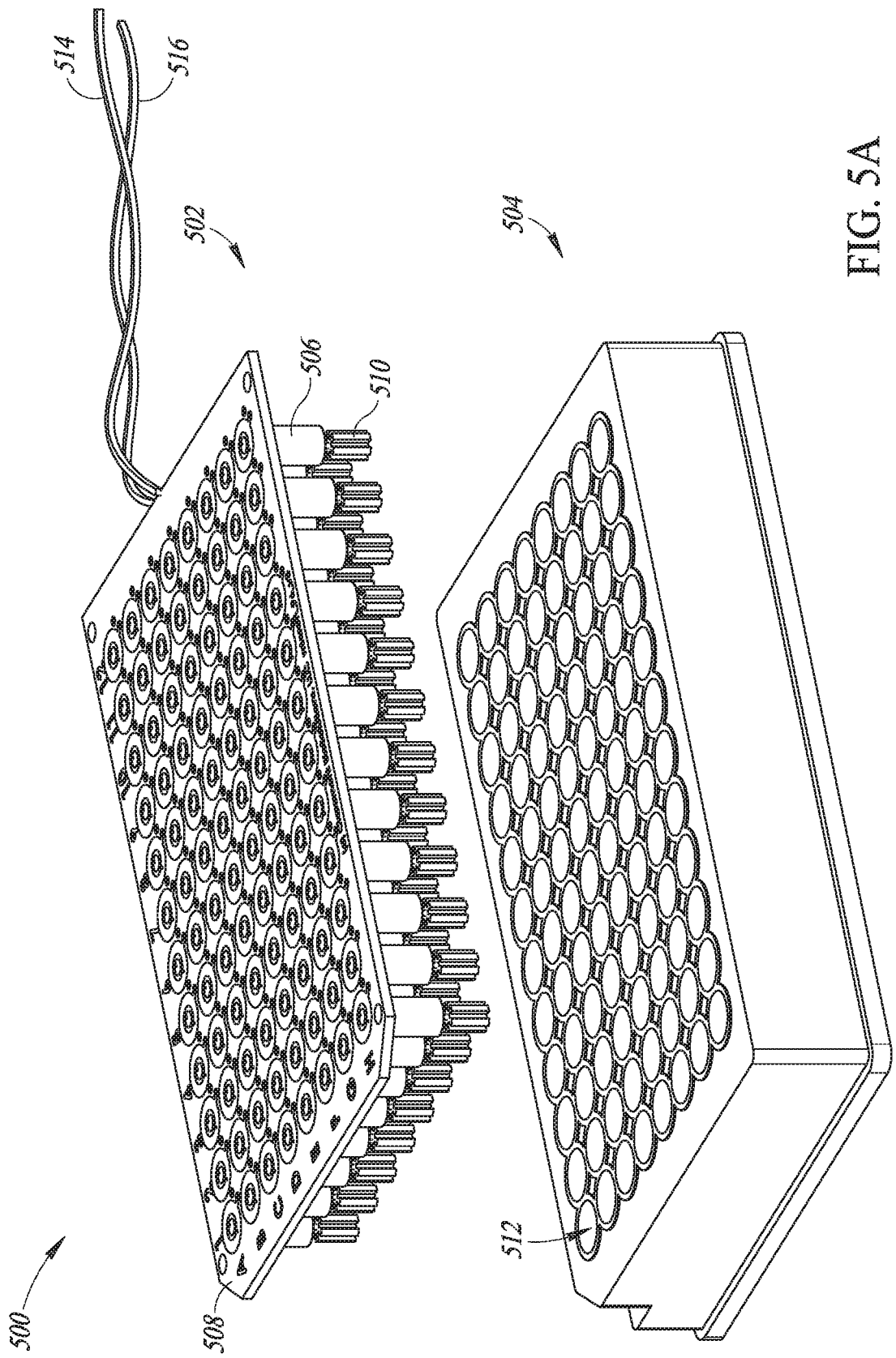
FIG. 5A is an isometric view of a spaced array of motors and a 96 well microtiter plate with the motors entering the wells of the microtiter plate from the top thereof, according to one illustrated implementation.
Figure 5B:
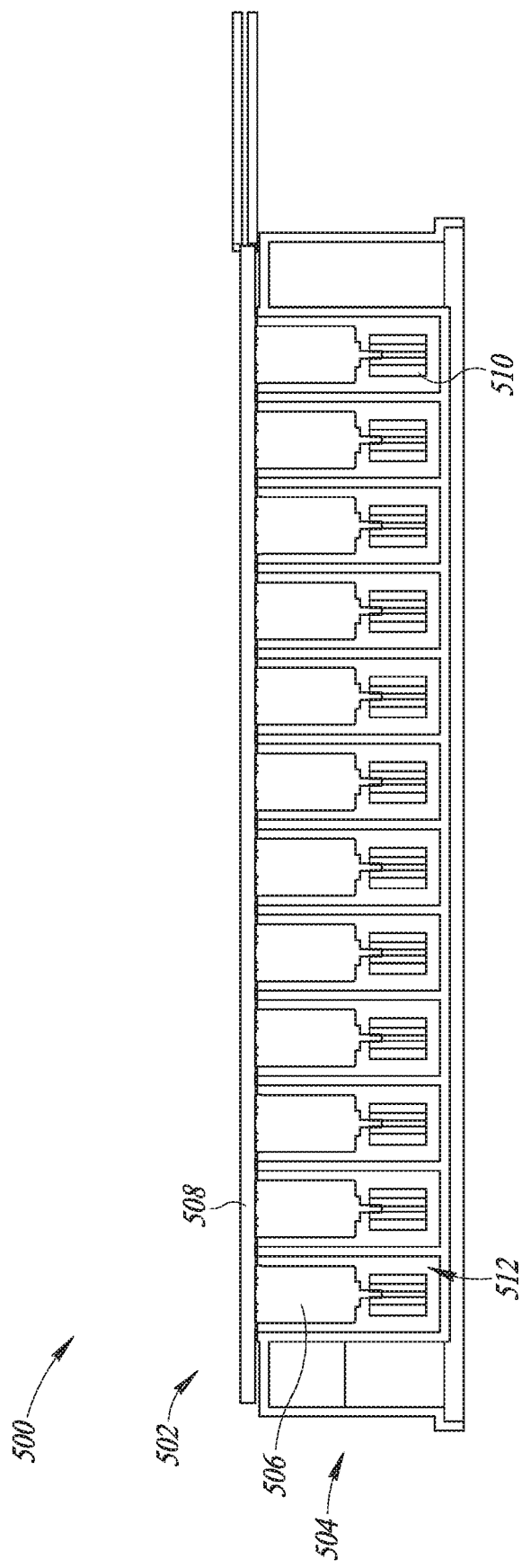
FIG. 5B is a sectional elevational view of the array of motors and the microtiter plate of FIG. 5A, according to one illustrated implementation.
Figure 5C:
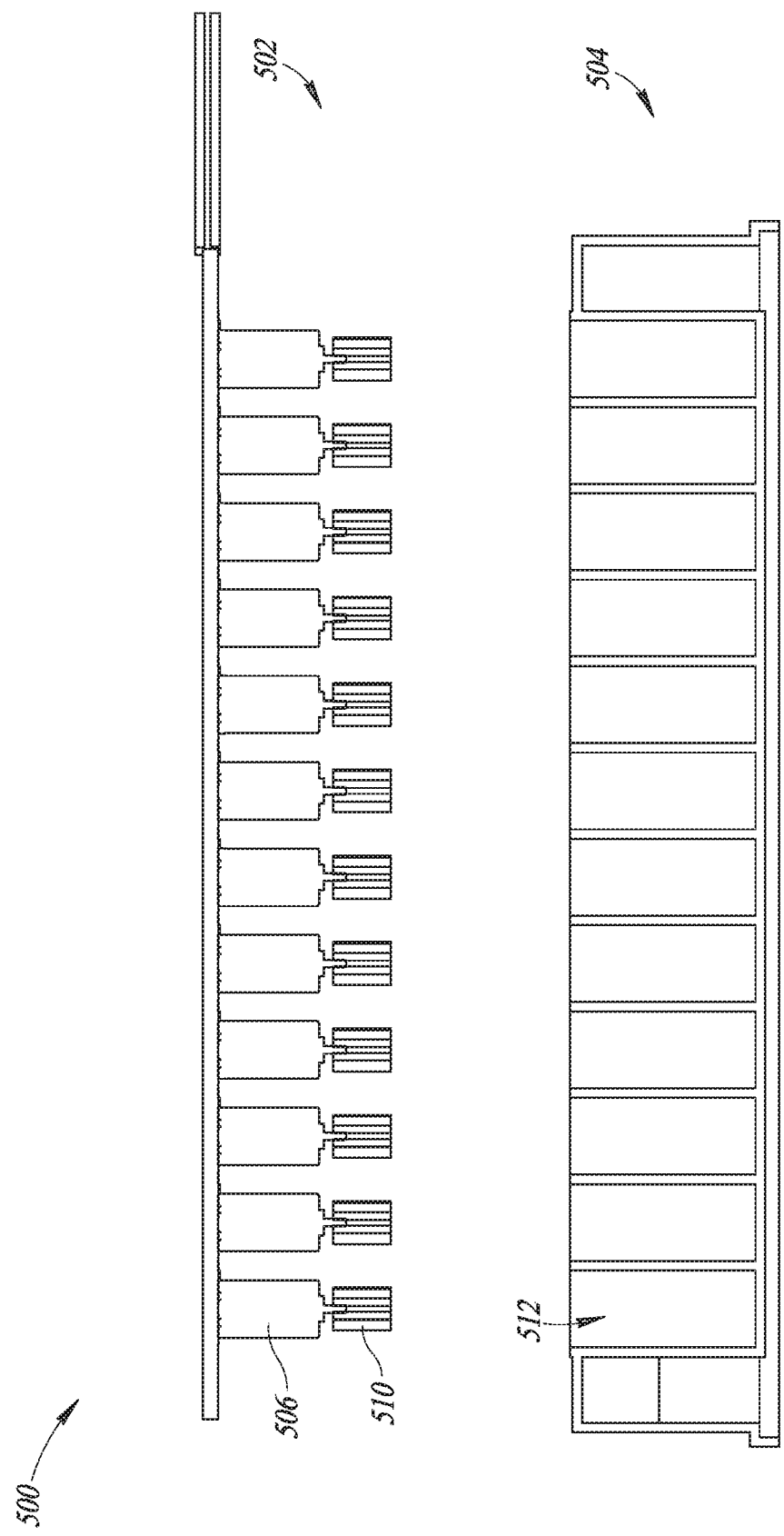
FIG. 5C is an elevational view of the array of motors and the microtiter plate of FIG. 5A, according to one illustrated implementation.

FIGS. 5A-5C show various views of a system 500 which includes a motor assembly 502 and a 96 well microtiter plate 504. In this implementation, the motor assembly 502 comprises 96 motors 506 that are each coupled to a motor carrier or plate 508. Each of the motors 506 is arranged with their respective impellers 510 facing downward toward the microtiter plate 504. In operation, samples and fluid may be disposed into each of the wells 512 of the microtiter plate 504. Then, as shown in FIG. 5B, the motor assembly 502 may be moved downward onto the microtiter plate 504 such that each of the impellers 510 is lowered at least partially into one of the wells 512. Wire leads 514 and 516 are attached to the motor carrier 508 of the motor assembly 502 to allow the simultaneous application of a voltage or voltage waveform to each of the micromotors so that the samples in the wells may be processed, as discussed above. Although in this example a 96 well format with 9 mm spacing is used, in other implementations other formats (e.g., 6 well format, 24 well format, 48 well format, 384 well format) and/or spacings (e.g., 4.5 mm, 6 mm, 6.35 mm, 9 mm, 10 mm, 12 mm, 12.7 mm, 13 mm, 13.5 mm, 16 mm, 18 mm, etc.), may be used.

The foregoing detailed description has set forth various implementations of the devices and/or processes via the use of block diagrams, schematics, and examples. Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. Those of skill in the art will recognize that many of the methods or algorithms set out herein may employ additional acts, may omit some acts, and/or may execute acts in a different order than specified.

The various embodiments described above can be combined to provide further embodiments. All of the commonly assigned US patent application publications, US patent applications, foreign patents, foreign patent applications and non-patent publications referred to in this specification and/or listed in the Application Data Sheet, including but not limited to U.S. Provisional Application No. 61/220,984 filed Jun. 26, 2009, U.S. Provisional Application No. 61/317,604 filed Mar. 25, 2010, U.S. Pat. No. 9,260,475 issued Feb. 16, 2016, PCT Publication No. WO2010/151705 published Dec. 29, 2010, U.S. Provisional Application No. 61/427,045 filed Dec. 23, 2010, U.S. Provisional Application No. 61/444,607 filed Feb. 18, 2011, U.S. Pat. No. 8,663,974 issued Mar. 4, 2014, U.S. Pat. No. 9,428,725 issued Aug. 30, 2016, U.S. Provisional Application No. 62/146,876 filed Apr. 13, 2015, U.S. application Ser. No. 14/993,953 filed Jan. 12, 2016, PCT Publication No. 2016/168301 published 20 Oct. 2016, U.S. Design application Ser. No. 29/583745 filed Nov. 8, 2016 and U.S. Provisional Application No. 62/454,500 filed Feb. 3, 2017, are incorporated herein by reference, in their entirety.

These and other changes can be made to the implementations in light of the above-detailed description. In general, in the following claims, the terms used should not be construed to limit the claims to the specific implementations disclosed in the specification and the claims, but should be construed to include all possible implementations along with the full scope of equivalents to which such claims are entitled. Accordingly, the claims are not limited by the disclosure.

The invention claimed is:

1. A system for homogenization and lysis of biological samples, the system comprising:
a plurality of chambers spaced apart from each other in an array along at least a first dimension, each of the plurality of chambers sized and dimensioned to receive fluid and a biological sample therein, wherein the plurality of chambers is defined by a housing which includes a plurality of downward-facing bottom openings therein, each of the bottom openings defining a respective one of the plurality of chambers;
a plurality of agitator devices each of which corresponds to one of the plurality of chambers, each of the agitator devices comprising a micromotor having a shaft and an impeller coupled to the shaft, wherein at least a portion of each of the plurality of agitator devices is reversibly and simultaneously receivable within respective ones of the downward-facing bottom openings in the plurality of chambers of the housing such that the shafts and the impellers of the micromotors are positioned within the respective chambers, and the micromotors are at least partially received in the respective downward-facing bottom openings in the chambers to seal the downward-facing bottom openings during use, and in operation each of the plurality of agitator devices selectively agitates the fluid and biological sample disposed in the corresponding one of the plurality of chambers; and
a motor carrier that supports the micromotors.

2. The system of claim 1 wherein the plurality of chambers are uniformly spaced apart from each other in a second dimension orthogonal to the first dimension.

3. The system of claim 2 wherein the plurality of chambers are uniformly spaced apart from each other in the first dimension by a first distance which extends between the center of adjacent chambers along the first dimension, and the plurality of chambers are uniformly spaced apart from each other in the second dimension by a second distance which extends between the center of adjacent chambers along the second dimension, wherein the first distance is different than the second distance.

4. The system of claim 1 wherein the plurality of chambers are uniformly spaced apart from each other in the first dimension by a first distance which extends between the center of adjacent chambers along the first dimension, and the first distance is equal to 4.5 millimeters (mm), 6 mm, 6.35 mm, 9 mm, 10 mm, 12 mm, 12.7 mm, 13 mm, 13.5 mm, 16 mm, or 18 mm.

5. The system of claim 1 wherein at least a portion of each of the plurality of agitator devices is selectively positionable within a corresponding one of the plurality of chambers.

6. The system of claim 1, further comprising:
a medium that includes a particulate material and a fluid, the medium disposed within at least some of the plurality of chambers.

7. The system of claim 6 wherein the particulate material includes at least one of ceramic, glass, zirconia, zirconia/silica, zirconium silicate, metal, plastic, nickel, tungsten, tungsten carbide, yttrium stabilized zirconia, or sand.

8. The system of claim 1, further comprising:
an electrical energy source electrically coupled to the micromotors, in operation the electrical energy source provides electrical energy to the each of the micromotors sufficient to rotate the shaft and the impeller in a manner sufficient to agitate the biological sample.

9. The system of claim 8 wherein each of the plurality of chambers comprises an upward-facing top opening that removably receives the fluid and the biological sample in the chamber.

10. A method of obtaining biological material, the method comprising:
introducing a plurality of samples containing the biological material into a respective plurality of chambers, the plurality of chambers spaced apart from each other in an array along at least a first dimension, each of the plurality of chambers sized and dimensioned to receive fluid and a biological sample therein, wherein the plurality of chambers is defined by a housing which includes a plurality of downward-facing bottom openings therein, each of the bottom openings defining a respective one of the plurality of chambers; and
simultaneously agitating the samples in each of the plurality of the chambers via a plurality of agitator devices supported by a motor carrier, each of the agitator devices comprising a micromotor having a shaft and an impeller coupled to the shaft, and at least a portion of each of the plurality of agitator devices is reversibly and simultaneously receivable at least partially within respective ones of the plurality of chambers through the bottom opening thereof, wherein the shafts and the impellers of the micromotors are positioned within the respective chambers, and the micromotors are at least partially received in the respective downward-facing bottom openings in the chambers to seal the downward-facing bottom openings during use.

11. The method of claim 10, further comprising:
positioning the plurality of agitator devices at least partially within respective ones of the plurality of chambers.

12. The method of claim 10, wherein simultaneously agitating the samples comprises:
applying electrical energy to each of the micromotors with an electrical energy source electrically coupled to the micromotors, the electrical energy sufficient to rotate the shaft and the impeller in a manner sufficient to agitate the biological samples disposed in the plurality of chambers.

* * * * *